(12) United States Patent
Elbaz et al.

(10) Patent No.: US 12,185,923 B2
(45) Date of Patent: Jan. 7, 2025

(54) UNIVERSAL LARYNGOSCOPE BLADE FOR BOTH CONVENTIONAL HANDLES AND FIBER-ILLUMINATED HANDLES

(71) Applicant: TELEFLEX MEDICAL INCORPORATED, Morrisville, NC (US)

(72) Inventors: Aviram Elbaz, Apex, NC (US); Nate DuBois, Durham, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 777 days.

(21) Appl. No.: 16/818,018

(22) Filed: Mar. 13, 2020

(65) Prior Publication Data

US 2020/0288961 A1 Sep. 17, 2020

Related U.S. Application Data

(60) Provisional application No. 62/818,484, filed on Mar. 14, 2019.

(51) Int. Cl.
*A61B 1/05* (2006.01)
*A61B 1/00* (2006.01)
(Continued)

(52) U.S. Cl.
CPC .......... *A61B 1/267* (2013.01); *A61B 1/00101* (2013.01); *A61B 1/00105* (2013.01);
(Continued)

(58) Field of Classification Search
CPC ............ A61B 1/00018; A61B 1/00032; A61B 1/00096; A61B 1/00101; A61B 1/00114;
(Continued)

(56) References Cited

U.S. PATENT DOCUMENTS 1,785,343 A 12/1930 Gilbert
2,289,226 A 7/1942 Von Foregger
(Continued)

FOREIGN PATENT DOCUMENTS

DE 2621232 11/1977
DE 20218560 5/2003
(Continued)

OTHER PUBLICATIONS

International Search Report and Written Opinion issued in PCT/US20/22564, dated Jun. 9, 2020.
(Continued)

*Primary Examiner* — Timothy J Neal
*Assistant Examiner* — William B Chou
(74) *Attorney, Agent, or Firm* — Baker Hostetler

(57) ABSTRACT

Universal laryngoscope blades and associated methods are disclosed. A universal laryngoscope blade includes a blade body. The blade body includes a first end and a second end. The second end is configured for insertion into a larynx. The universal laryngoscope blade further includes a viewer connected to the blade body. The viewer is configured to function independently from each of a conventional handle and a fiber-illuminated handle. The universal laryngoscope blade further includes a blade fitting disposed at the first end of the blade body. The blade fitting is removably connectable to, one at a time, each of a hook-on fitting of the conventional handle and a hook-on fitting of the fiber-illuminated handle. The hook-on fitting of the conventional handle has at least one physical dimension that is different from at least one physical dimension of the hook-on fitting of the fiber-illuminated handle.

21 Claims, 13 Drawing Sheets

(51) Int. Cl.
 *A61B 1/06* (2006.01)
 *A61B 1/07* (2006.01)
 *A61B 1/267* (2006.01)

(52) U.S. Cl.
 CPC ...... *A61B 1/00114* (2013.01); *A61B 1/00124* (2013.01); *A61B 1/00128* (2013.01); *A61B 1/05* (2013.01); *A61B 1/0676* (2013.01); *A61B 1/07* (2013.01)

(58) Field of Classification Search
 CPC ..... A61B 1/00124; A61B 1/05; A61B 1/0676; A61B 1/07; A61B 1/267
 See application file for complete search history.

(56) References Cited

U.S. PATENT DOCUMENTS

| | | |
|---|---|---|
| 2,433,705 A | 12/1947 | Palmeter |
| 2,630,114 A | 3/1953 | Hart |
| 2,646,036 A | 7/1953 | Allyn |
| 2,854,004 A | 9/1958 | Durrant |
| 2,911,968 A | 11/1959 | Schueler |
| 3,426,749 A | 2/1969 | Jephcott |
| 3,507,272 A | 4/1970 | Laerdal |
| 3,595,222 A | 7/1971 | Vellacott |
| 3,598,113 A | 8/1971 | Moore |
| 3,638,644 A | 2/1972 | Reick |
| 3,766,909 A | 10/1973 | Ozbey |
| 3,771,514 A | 11/1973 | Huffman et al. |
| 3,779,655 A | 12/1973 | Toyota |
| 3,826,248 A | 7/1974 | Gobels |
| 3,856,001 A | 12/1974 | Phillips |
| 3,986,854 A | 10/1976 | Scrivo et al. |
| 4,037,588 A | 7/1977 | Heckele |
| 4,112,933 A | 9/1978 | Moses |
| 4,124,939 A | 11/1978 | Onoue |
| 4,126,127 A | 11/1978 | May |
| 4,273,112 A | 6/1981 | Heine et al. |
| 4,295,465 A | 10/1981 | Racz et al. |
| 4,337,761 A | 7/1982 | Upsher |
| 4,360,008 A | 11/1982 | Corazzelli, Jr. |
| 4,406,280 A | 9/1983 | Upsher |
| 4,425,709 A | 1/1984 | Quenzi |
| 4,437,458 A | 3/1984 | Upsher |
| 4,488,655 A | 12/1984 | Itsubo et al. |
| 4,519,514 A | 5/1985 | Agbay et al. |
| 4,527,553 A | 7/1985 | Upsher |
| 4,556,052 A | 12/1985 | Muller |
| 4,557,256 A | 12/1985 | Bauman |
| 4,565,187 A | 1/1986 | Soloway |
| 4,570,614 A | 2/1986 | Bauman |
| 4,579,108 A | 4/1986 | Bauman |
| 4,583,527 A | 4/1986 | Musicant et al. |
| 4,596,239 A | 6/1986 | Bauman |
| 4,669,449 A | 6/1987 | Bauman |
| 4,679,547 A | 7/1987 | Bauman |
| 4,694,822 A | 9/1987 | Bauman |
| 4,694,969 A | 9/1987 | Granat |
| 4,862,772 A | 9/1989 | Piperato |
| 4,878,486 A | 11/1989 | Slater |
| 4,884,558 A | 12/1989 | Gorski et al. |
| 4,924,855 A | 5/1990 | Salerno et al. |
| 4,930,495 A | 6/1990 | Upsher |
| 4,958,624 A | 9/1990 | Stone et al. |
| 4,972,825 A | 11/1990 | Vescovo, Jr. |
| 5,036,835 A | 8/1991 | Filli |
| 5,038,766 A | 8/1991 | Parker |
| 5,060,633 A | 10/1991 | Gibson |
| 5,065,738 A | 11/1991 | Van Dam |
| 5,095,624 A | 3/1992 | Ennis |
| 5,169,257 A | 12/1992 | Liou |
| 5,178,131 A | 1/1993 | Upsher |
| D337,384 S | 7/1993 | Schucman |
| 5,305,932 A | 4/1994 | Iseli |
| 5,355,870 A | 10/1994 | Lacy |
| 5,443,058 A | 8/1995 | Ough |
| 5,501,651 A | 3/1996 | Bauman |
| 5,529,570 A | 6/1996 | Storz |
| 5,575,758 A | 11/1996 | Easterbrook, III |
| 5,651,760 A | 7/1997 | Upsher |
| 5,678,718 A | 10/1997 | Morris et al. |
| 5,685,079 A | 11/1997 | Brothers et al. |
| 5,702,351 A | 12/1997 | Bar-Or et al. |
| 5,727,682 A | 3/1998 | Abidin et al. |
| 5,769,094 A | 6/1998 | Jenkins, Jr. et al. |
| D399,957 S | 10/1998 | Chernov et al. |
| 5,873,818 A | 2/1999 | Rothfels |
| 5,879,304 A * | 3/1999 | Shuchman ......... A61B 1/00103 600/193 |
| D413,977 S | 9/1999 | Cranton et al. |
| 5,984,863 A | 11/1999 | Ansari |
| 6,013,026 A | 1/2000 | Krauter et al. |
| 6,102,851 A | 8/2000 | Mellin |
| 6,123,666 A | 9/2000 | Wrenn et al. |
| 6,139,491 A | 10/2000 | Heine et al. |
| 6,213,937 B1 * | 4/2001 | Vivenzio ............. A61B 1/07 600/199 |
| 6,248,061 B1 | 6/2001 | Cook, Jr. |
| 6,354,993 B1 | 3/2002 | Kaplan et al. |
| 6,394,295 B2 | 5/2002 | Claude |
| 6,471,643 B1 | 10/2002 | Henderson |
| 6,626,829 B1 | 9/2003 | Skaggs |
| 6,666,819 B2 | 12/2003 | Heine et al. |
| 6,719,688 B2 | 4/2004 | Pecherer et al. |
| 6,735,825 B1 | 5/2004 | Berman et al. |
| 6,890,298 B2 | 5/2005 | Berci et al. |
| 6,918,184 B2 | 7/2005 | Glesser |
| 6,964,637 B2 | 11/2005 | Dalle et al. |
| D512,778 S | 12/2005 | Ashraf |
| 7,007,392 B2 | 3/2006 | Ping |
| 7,039,975 B1 | 5/2006 | Liao |
| 7,044,909 B2 | 5/2006 | Berci et al. |
| 7,128,710 B1 | 10/2006 | Cranton et al. |
| 7,214,184 B2 | 5/2007 | McMorrow |
| D544,601 S | 6/2007 | Iqbal |
| D554,255 S | 10/2007 | Iqbal |
| D559,982 S | 1/2008 | Iqbal |
| D562,452 S | 2/2008 | Iqbal |
| 7,338,440 B1 | 3/2008 | Smith |
| D581,532 S | 11/2008 | Cranton et al. |
| 7,608,040 B1 | 10/2009 | Dunst |
| 7,611,459 B2 | 11/2009 | Geist et al. |
| D609,808 S | 2/2010 | Tenger et al. |
| 7,736,304 B2 | 6/2010 | Pecherer |
| 7,771,350 B2 | 8/2010 | Geist et al. |
| 7,824,331 B1 * | 11/2010 | Cranton ............. A61B 1/267 600/190 |
| D628,693 S | 12/2010 | Thuenker |
| D629,516 S | 12/2010 | Firmin |
| D629,517 S | 12/2010 | Jauch et al. |
| D630,735 S | 1/2011 | Behrbohm |
| D630,738 S | 1/2011 | Tenger et al. |
| D630,739 S | 1/2011 | Tenger et al. |
| D630,744 S | 1/2011 | Tenger et al. |
| D631,156 S | 1/2011 | Halder et al. |
| D631,158 S | 1/2011 | Doerges |
| D632,783 S | 2/2011 | Maesarapu |
| 7,878,973 B2 | 2/2011 | Yee et al. |
| D634,008 S | 3/2011 | Tenger et al. |
| 7,909,758 B2 | 3/2011 | Shapiro |
| 7,909,759 B2 | 3/2011 | Pecherer |
| D643,921 S | 8/2011 | Davila |
| D645,146 S | 9/2011 | Lee |
| 8,142,353 B2 | 3/2012 | Pecherer et al. |
| 8,162,826 B2 | 4/2012 | Pecherer et al. |
| D659,246 S | 5/2012 | McGrath et al. |
| 8,251,898 B2 | 8/2012 | Pecherer |
| 8,267,856 B2 | 9/2012 | Anders |
| D669,680 S | 10/2012 | Goldstein |
| 8,414,481 B2 | 4/2013 | Hakanen et al. |
| 8,512,234 B2 | 8/2013 | Grey et al. |
| 8,628,879 B2 | 1/2014 | Pecherer et al. |
| 8,702,598 B2 | 4/2014 | Geist et al. |
| 8,715,171 B2 | 5/2014 | Pastron |

(56) References Cited

U.S. PATENT DOCUMENTS

| | | |
|---|---|---|
| 8,979,745 B2 | 3/2015 | Swift |
| 8,998,804 B2 | 4/2015 | Boedeker |
| 9,078,614 B2 | 7/2015 | Bird |
| D738,501 S | 9/2015 | Renner |
| D739,017 S | 9/2015 | Renner |
| D745,669 S | 12/2015 | Swift |
| D746,451 S | 12/2015 | Chen |
| 9,198,567 B1 | 12/2015 | Dube |
| D748,255 S | 1/2016 | McGrath et al. |
| 9,314,151 B2 | 4/2016 | McGrath et al. |
| 9,357,904 B2 | 6/2016 | Wu |
| 9,414,743 B2 | 8/2016 | McGrath |
| 9,510,745 B2 | 12/2016 | Geist et al. |
| 9,622,651 B2 | 4/2017 | Miller et al. |
| 9,662,001 B2 | 5/2017 | McGrath et al. |
| D791,943 S | 7/2017 | Cook |
| 9,737,202 B2 | 8/2017 | McGrath |
| 10,244,922 B2 | 4/2019 | Elbaz et al. |
| D862,696 S | 10/2019 | Elbaz et al. |
| D863,555 S | 10/2019 | Elbaz et al. |
| 10,588,498 B2 | 3/2020 | Dan et al. |
| 2001/0014768 A1 | 8/2001 | Kaplan et al. |
| 2002/0082477 A1 | 6/2002 | Kim |
| 2002/0082478 A1 | 6/2002 | McGrath |
| 2002/0087050 A1 | 7/2002 | Rudischhauser et al. |
| 2003/0092967 A1 | 5/2003 | Fourie et al. |
| 2003/0120131 A1 | 6/2003 | Pecherer et al. |
| 2004/0034281 A1 | 2/2004 | Cartledge et al. |
| 2004/0122292 A1 | 6/2004 | Dey et al. |
| 2004/0127770 A1 | 7/2004 | McGrath |
| 2004/0129741 A1 | 7/2004 | Stoneberg et al. |
| 2004/0215062 A1 | 10/2004 | Dalle et al. |
| 2005/0043590 A1 | 2/2005 | Mazzei et al. |
| 2005/0090712 A1 | 4/2005 | Cubb |
| 2005/0234303 A1 | 10/2005 | McMorrow |
| 2005/0240081 A1 | 10/2005 | Eliachar |
| 2006/0079734 A1 | 4/2006 | Miyagi |
| 2006/0100483 A1 | 5/2006 | Sundet et al. |
| 2006/0189847 A1 | 8/2006 | Yee et al. |
| 2007/0093693 A1 | 4/2007 | Geist et al. |
| 2007/0129606 A1 | 6/2007 | Pecherer |
| 2007/0129607 A1 | 6/2007 | Ashfaque |
| 2007/0161863 A1 | 7/2007 | Bentt |
| 2007/0167686 A1 | 7/2007 | McGrath |
| 2007/0179342 A1 | 8/2007 | Miller et al. |
| 2007/0197873 A1 | 8/2007 | Birnkrant |
| 2008/0045801 A1 | 2/2008 | Shalman et al. |
| 2008/0051628 A1 | 2/2008 | Pecherer et al. |
| 2008/0096099 A1 | 4/2008 | Pecherer et al. |
| 2008/0188717 A1 | 8/2008 | Chen et al. |
| 2008/0300464 A1 | 12/2008 | Dhingra et al. |
| 2009/0065007 A1 | 3/2009 | Wilkinson et al. |
| 2009/0099421 A1 | 4/2009 | Shalman et al. |
| 2009/0112067 A1 | 4/2009 | Baker |
| 2009/0187078 A1 | 7/2009 | Dunlop |
| 2009/0209816 A1 | 8/2009 | Gunther Nielsen et al. |
| 2009/0270684 A1 | 10/2009 | Nielsen et al. |
| 2009/0318767 A1 | 12/2009 | Tenger et al. |
| 2010/0004514 A1 | 1/2010 | Shalman et al. |
| 2010/0022843 A1 | 1/2010 | Pecherer et al. |
| 2010/0041953 A1 | 2/2010 | Pecherer et al. |
| 2010/0191062 A1 | 7/2010 | Kieffer |
| 2010/0198017 A1 | 8/2010 | Raspallo |
| 2010/0217085 A1 | 8/2010 | Williams et al. |
| 2010/0258563 A1 | 10/2010 | Parrinello et al. |
| 2010/0261968 A1 | 10/2010 | Nearman et al. |
| 2011/0060190 A1 | 3/2011 | Pecherer |
| 2011/0077466 A1 | 3/2011 | Rosenthal |
| 2011/0245609 A1* | 10/2011 | Laser .................. A61B 1/00052 600/109 |
| 2012/0055470 A1 | 3/2012 | Pecherer et al. |
| 2013/0018227 A1* | 1/2013 | Schoonbaert ...... A61B 1/00052 600/188 |
| 2013/0041227 A1* | 2/2013 | Chan ................. A61M 16/0488 600/199 |
| 2014/0202459 A1 | 7/2014 | Iqbal |
| 2014/0371536 A1 | 12/2014 | Miller et al. |
| 2016/0000305 A1 | 1/2016 | Elbaz et al. |
| 2016/0128548 A1* | 5/2016 | Lai ..................... A61B 1/00105 600/188 |
| 2016/0317005 A1 | 11/2016 | Dunlop |
| 2016/0317008 A1 | 11/2016 | McGrath et al. |
| 2017/0020384 A1 | 1/2017 | Fitzgerald et al. |
| 2017/0079518 A1 | 3/2017 | Elbaz et al. |
| 2017/0150878 A1 | 6/2017 | Swift |
| 2017/0202447 A1* | 7/2017 | Pecherer ............ A61B 1/00066 |
| 2018/0008137 A1 | 1/2018 | Poormand |
| 2018/0168433 A1* | 6/2018 | Meyer ................. A61B 1/00016 |
| 2019/0053698 A1* | 2/2019 | Young ................... A61B 1/267 |
| 2019/0133430 A1* | 5/2019 | Inglis ................. A61B 1/00052 |

FOREIGN PATENT DOCUMENTS

| | | | |
|---|---|---|---|
| DE | 102011018688 | 10/2012 | |
| EP | 0184588 | 6/1986 | |
| EP | 0653180 | 10/1998 | |
| GB | 685741 | 1/1953 | |
| GB | 806467 | 12/1958 | |
| GB | 2385793 | 9/2003 | |
| GB | 2491189 A * | 11/2012 | ......... A61B 1/00032 |
| GB | 2537118 | 10/2016 | |
| JP | 08-024221 A | 1/1996 | |
| JP | 09-140670 A | 6/1997 | |
| WO | 83/01373 | 4/1983 | |
| WO | 88/00021 | 1/1988 | |
| WO | 99/44490 | 9/1999 | |
| WO | 2005/082231 | 9/2005 | |
| WO | 2005/107575 | 11/2005 | |
| WO | 2006/131770 | 12/2006 | |
| WO | 2009/066078 | 5/2009 | |
| WO | 2016/092134 | 6/2016 | |
| WO | 2018/023138 | 2/2018 | |
| WO | 2020/050922 | 3/2020 | |

OTHER PUBLICATIONS

Hilbro brochure, Green System Fiber Optic Laryngoscope, Interchangeable Light Guide Insert, Oct. 2001.

Medizintechnik KaWe Germany, Laryngoscopes Catalog, Megalight F.O.

Flexicare BitePro Solo product webpage (https://www.flexicare.com/products/airway-management/single-use-laryngos-copes/britepro-solo).

* cited by examiner

SECTION B-B

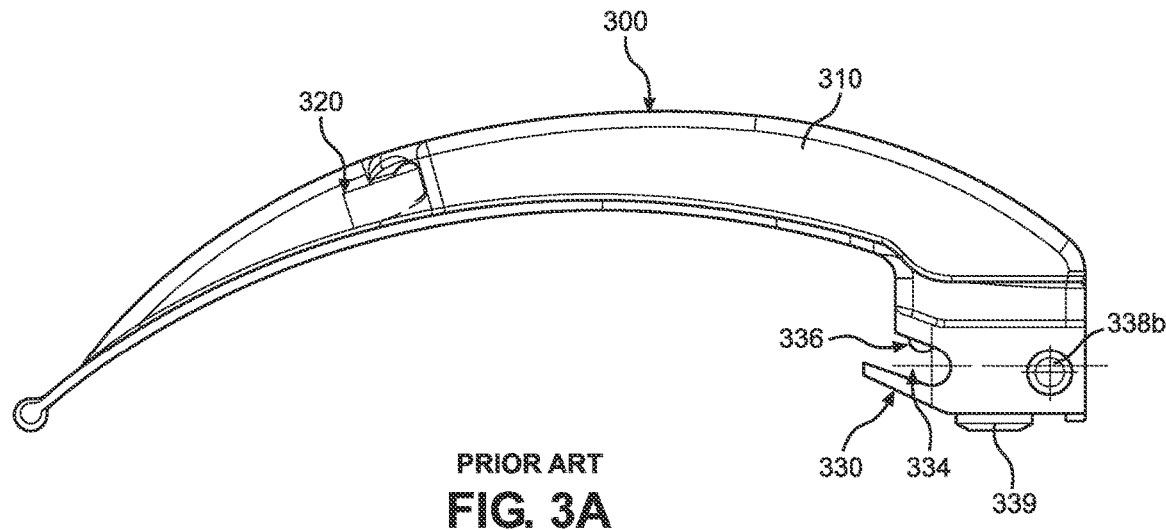
PRIOR ART
FIG. 3A
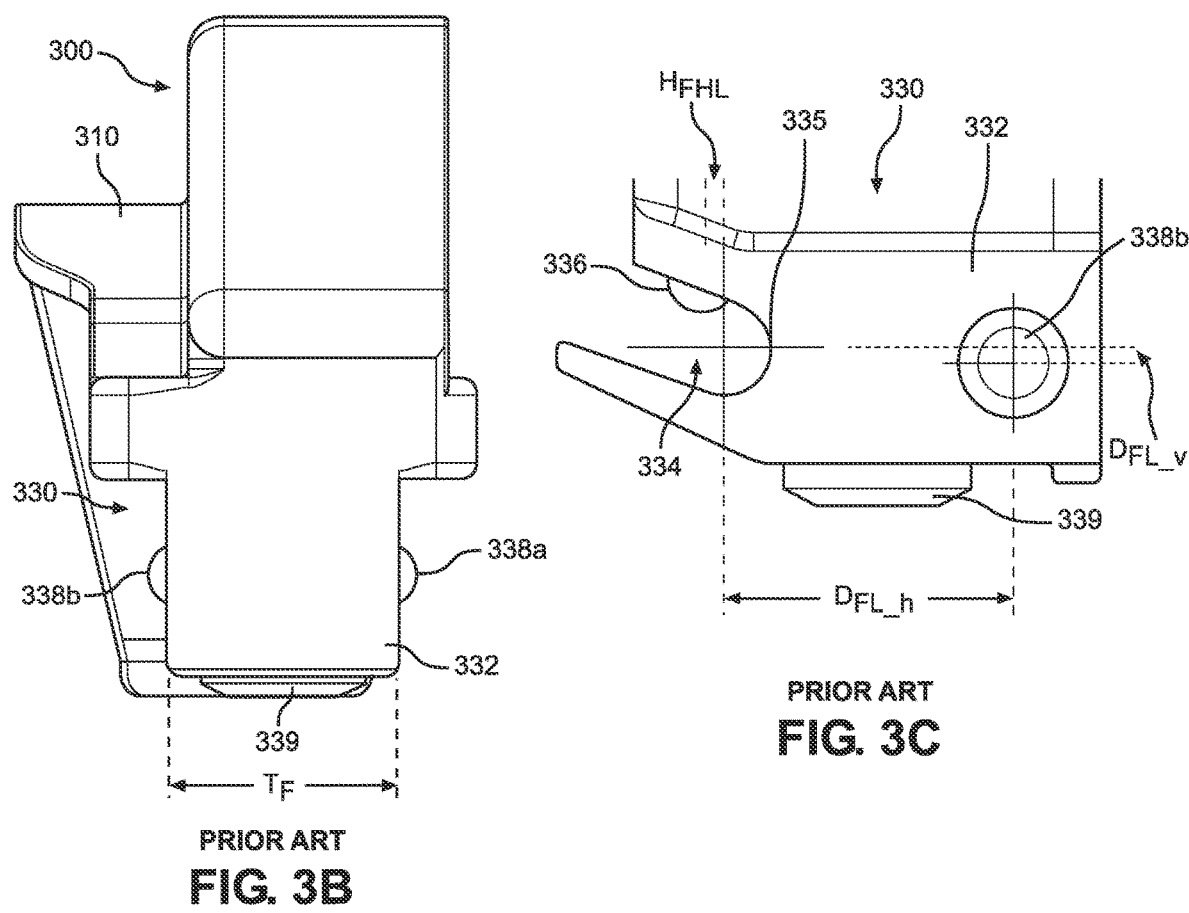
PRIOR ART
FIG. 3B
PRIOR ART
FIG. 3C

SECTION A-A

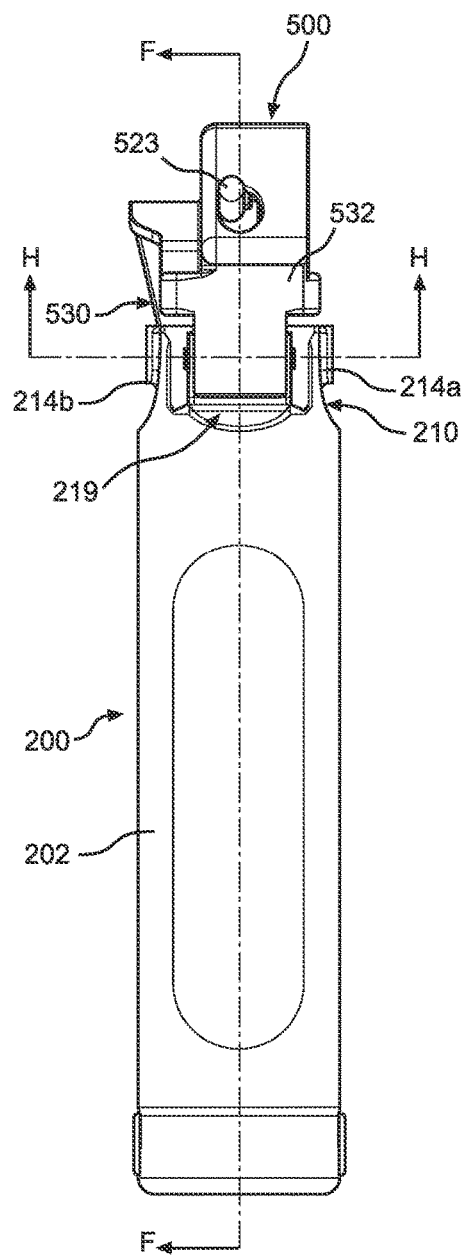
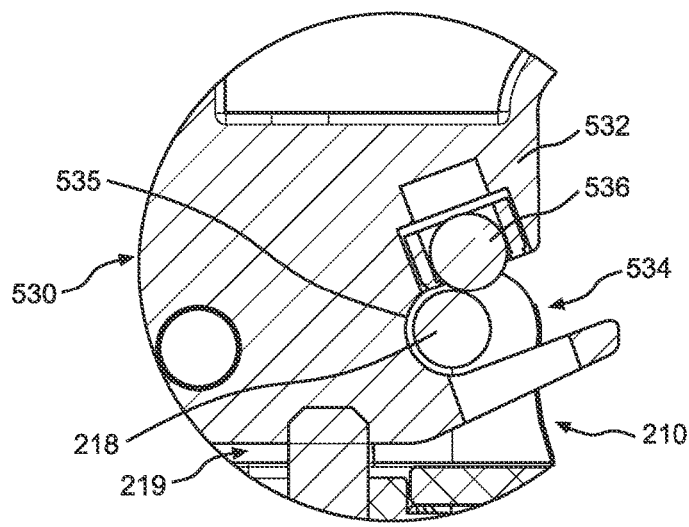
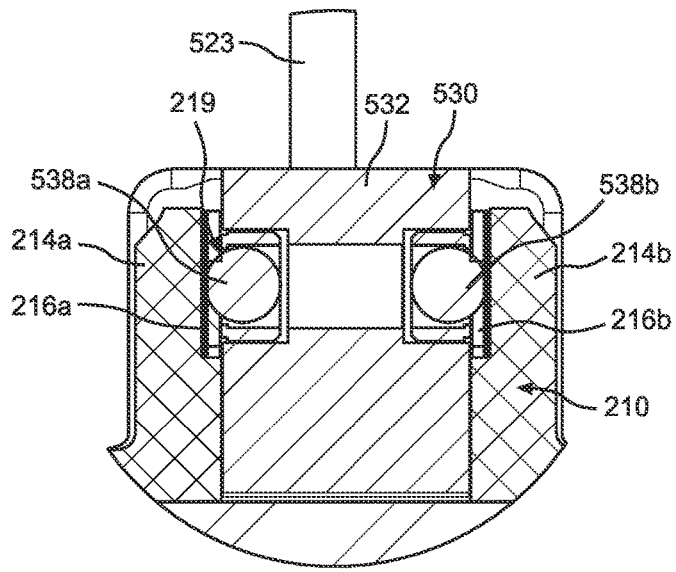
FIG. 9A
FIG. 9B
FIG. 9C

UNIVERSAL LARYNGOSCOPE BLADE FOR BOTH CONVENTIONAL HANDLES AND FIBER-ILLUMINATED HANDLES

CROSS-REFERENCE TO RELATED APPLICATIONS

This application claims priority to U.S. Provisional Patent Application No. 62/818,484, filed Mar. 14, 2019, the content of which is incorporated herein by reference in its entirety.

TECHNICAL FIELD

The invention relates to the field of laryngoscopes in general, and particularly for universal laryngoscope blades.

BACKGROUND

Laryngoscopes typically include a lamp that emits light to illuminate a field of view during intubation. The lamp for illuminating the larynx during use is attached either to the laryngoscope blade, or is provided in the handle and the blade includes a light guide that guides the light produced in the handle. Known laryngoscope blades that include the lamp are referred to herein as conventional blades. Known laryngoscope blades that include a light guide for guiding light produced from a lamp provided in the handle are referred to herein as fiber-illuminated blades.

FIGS. 1A-C show views of an exemplary known conventional blade 100. FIG. 1A shows a side view of the conventional blade 100. FIG. 1B shows a rear view of the convention blade. FIG. 1C shows a magnified side view of the blade fitting 130 of the conventional blade 100. Unless otherwise indicated, direction terms such as "top," "bottom," "front," "rear," "above," "below," "vertical," "horizontal," etc., when used to describe the position of a structure shown in the figures, are directed to the respective direction of the structure as oriented in the figures. For example, the blade fitting 130 of the conventional blade 100 (described in further detail below) is provided on the bottom of the conventional blade 100, as oriented in FIGS. 1A-C. Nevertheless, the direction terms used herein do not necessarily correspond to the orientation of the structure with respect to a user or a patient during intended use.

The conventional blade 100 includes a blade body 110, a lamp 120, and a blade fitting 130. The blade fitting 130 includes a body 132, a lock, an electrical contact 137, and a hinge slot 134. As shown in FIG. 1B, the body 132 has a thickness $T_C$. The lock includes a hinge lock 136 disposed within a bottom surface of the hinge slot 134. The lock also includes a side lock 138 provided on a side of the body 132. A center point of the side lock 138 is indicted at the intersection of side lock crosshairs, as shown in FIG. 1C. The hinge lock 136 and the side lock 138 are detent mechanisms. The electrical contact 137 is provided on a bottom of the body 132. The electrical contact 137 is in electrical communication with the lamp 120 via one or more wires that supply power to the lamp 120. The hinge slot 134 extends into the body 132 at an angle from a front the body 132 towards a central region of the body 132 and terminates at a bearing surface 135. The bearing surface 135 has a semicircular shape having a diameter and a virtual center point, indicated at the intersection of hinge slot crosshairs shown in FIG. 1C, about which the bearing surface 135 forms the semicircular shape.

With reference to the magnified side view of the blade fitting 130 of the conventional blade 100 shown in FIG. 1C, the center point of the side lock 138 is spaced from the virtual center point of the semicircular bearing surface 135 by a distance having a horizontal distance component $D_{CL\_h}$, and a vertical distance component $D_{CL\_v}$. The center point of the side lock 138 is spaced rearwardly from the virtual center point of the semicircular bearing surface 135 by the horizontal distance component $D_{CL\_h}$, and is spaced below the virtual center point of the bearing surface 135 by the vertical distance component $D_{CL\_v}$.

FIGS. 2A-C show views of an exemplary known conventional handle 200. FIG. 2A shows a perspective view of the conventional handle 200. FIG. 2B shows a top view of a hook-on fitting 210 of the conventional handle 200. FIG. 2C shows a cut-away side view of the hook-on fitting 210 of the conventional handle 200 taken along section B-B of FIG. 2B.

The conventional handle 200 includes a grip 202 and a hook-on fitting 210 disposed at a top of the grip 202. The grip 202 is configured to be grasped by the hand of a user of the laryngoscope. The conventional handle 200 also includes one or more batteries disposed within an interior of the grip 202. The one or more batteries serve as a power source for the lamp 120 of the conventional blade 100.

The hook-on fitting 210 of the conventional handle 200 is specifically designed for attachment to the blade fitting 130 of the conventional blade 100, and vice versa. The hook-on fitting 210 includes an electrical contact 212, first and second side supports 214a, 214b, and a hinge pin 218. The electrical contact 212 is in electrical communication with the batteries via one or more wires that supply power to the electrical contact 212. The electrical contact 212 is configured to supply power to the electrical contact 137 of the blade fitting 130 of the conventional blade 100 when the conventional blade 100 is engaged with the conventional handle 200 in an operating position.

The first and second side supports 214a, 214b extend vertically from the top of the grip 202. The first and second side supports 214a, 214b extend parallel to each other and are spaced apart from each other. The space bounded within the top of the grip 202 and the first and second side supports 214a, 214b forms a seat 219. The seat 219 has a width $W_C$ between the first and second side supports 214a, 214b. The width $W_C$ is greater than the thickness $T_C$ of the body 132 of the blade fitting 130 such that the seat 219 is configured to receive the body 132 of the blade fitting 130 therein.

The hinge pin 218 is attached to (i.e., extends through) the front of each of the first and second side supports 214a, 214b and extends across the seat 219. The hinge pin 218 is a cylinder having a diameter $d_C$. The diameter $d_C$ is less than the diameter of the semicircular bearing surface 135 of the blade fitting 130 such that the hinge pin 218 is configured to be received within, and be rotatably supported by, the hinge slot 134 of the conventional blade 100. The hinge lock 136 is configured to lock the hinge pin 218 within the hinge slot 134.

At least one of the side supports includes a lock slot protruding into a seat-facing side of the respective side support. For example, the first side support 214a includes a first lock slot 216a and the second side support 214b includes a second lock slot 216b (shown in FIG. 9C). The lock slot is configured to receive the side lock 138 of the blade fitting 130 to hold the body 132 within the seat 219. To ensure that the side lock 138 fits within the lock slot when the conventional blade 100 is engaged with the conventional handle 200, a center of each respective lock slot is spaced from a center point of the hinge pin 218, designated by the intersection of the hinge pin crosshairs shown in FIG. 2C, by a distance having a horizontal distance component $D_{CLS\_h}$, and a vertical distance component $D_{CLS\_v}$. The center of each respective lock slot is spaced rearwardly from the center point of the hinge pin 218 by the horizontal distance component $D_{CLS\_h}$, and is spaced below the center point of the hinge pin 218 by the vertical distance component $D_{CLS\_v}$.

The blade fitting 130 of the conventional blade 100 is configured to engage with hook-on fitting 210 of the conventional handle 200 to lock the conventional blade 100 within the conventional handle 200 in an operating position, in which the laryngoscope is ready-for-use. To place the conventional blade 100 in the operating position, the blade fitting 130 is first attached to the hook-on fitting 210. The blade fitting 130 is attached to the hook-on fitting 210 by placing the hinge pin 218 of the hook-on fitting 210 within the hinge slot 134 of the blade fitting 130 and providing relative movement between the hinge pin 218 and the hinge slot 134 until the hinge pin 218 abuts against the semicircular bearing surface 135 of the hinge slot 134 and is locked therein by the hinge lock 136. Relative rotational movement is provided between the conventional blade 100 and the conventional handle 200 such that the hinge slot 134 and the hinge pin 218 are rotated relative to one and other until the body 132 of the blade fitting 130 slides within the seat 219 of the hook-on fitting 210. After the body 132 of the blade fitting 130 is fully received within the seat 219 of the hook-on fitting 210, the side lock 138 of the blade fitting 130 engages with the lock slot of the hook-on fitting 210. The conventional blade 100 is thus locked within the conventional handle 200 in the operating position. In the operating position, the electrical contact 137 of the blade fitting 130 is engaged with the electrical contact 212 of the hook-on fitting 210, and the laryngoscope is ready-for-use.

FIGS. 3A-C show views of an exemplary known fiber-illuminated blade 300. FIG. 3A shows a side view of the fiber-illuminated blade 300. FIG. 3B shows a rear view of the fiber-illuminated blade 300. FIG. 3C shows a magnified side view of the blade fitting 330 of the fiber-illuminated blade 300.

The fiber-illuminated blade 300 includes a blade body 310, a light guide 320, and a blade fitting 330. The blade fitting 330 includes a body 332, a lock, a light guide interface 339, and a hinge slot 334. As shown in FIG. 3B, the body 332 has a thickness $T_F$. The lock includes a hinge lock 336 disposed within a top surface of the hinge slot 334. The lock also includes first and second side locks 338a, 338b respectively provided on opposite sides of the body 332. A center point of the second side lock 338b is indicted at the intersection of side lock crosshairs, as shown in FIG. 3C. The hinge lock 336 and the first and second side locks 338a, 338b are detent mechanisms. The light guide interface 339 is an end of the light guide 320 that is provided on a bottom of the body 332. The light guide interface 339 is configured to interface with an optical pathway 412 of a fiber-illuminated handle 400 (described below) to receive light transmitted from a lamp disposed within the fiber-illuminated handle 400. The hinge slot 334 extends into the body 332 at an angle from a front the body 332 towards a central region of the body 332 and terminates at a bearing surface 335. The bearing surface 335 has semicircular shape having a diameter and a virtual center point, indicated by the intersection of hinge slot crosshairs shown in FIG. 3C, about which the bearing surface 335 forms the semicircular shape.

With reference to the magnified side view of the blade fitting 330 of the fiber-illuminated blade 300 shown in FIG. 3C, a center of the hinge lock 336 is spaced forwardly from the virtual center of the semicircular bearing surface 335 by a horizontal distance $H_{FHL}$. The center point of the second side lock 338b is spaced from the virtual center point of the semicircular bearing surface 335 by a distance having a horizontal distance component $D_{FL\_h}$, and a vertical distance component $D_{FL\_v}$. The center point of the second side lock 338b is spaced rearwardly from the virtual center point of the semicircular bearing surface 335 by the horizontal distance component $D_{FL\_h}$, and is spaced below the virtual center point of the bearing surface 335 by the vertical distance component $D_{FL\_v}$. A center point of the first side lock 338b is provided at a corresponding position at the other side surface of the body 332 with respect to the virtual center point of the semicircular bearing surface 335 such that the first and second side locks 338a, 338b are spaced the same distance from the virtual center point of the semicircular bearing surface 335.

FIGS. 4A-C show views of an exemplary known fiber-illuminated handle 400. FIG. 4A shows a perspective view of the fiber-illuminated handle 400. FIG. 4B shows a top view of the hook-on fitting 410 of the fiber-illuminated handle 400. FIG. 4C shows a cut-away side view of the hook-on fitting 410 of the fiber-illuminated handle 400 taken along section A-A of FIG. 4B.

The fiber-illuminated handle 400 includes a grip 402 and a hook-on fitting 410 disposed at a top of the grip 402. The grip 402 is configured to be grasped by the hand of a user of the laryngoscope. The fiber-illuminated handle 400 also includes one or more batteries, the lamp, and an optical pathway 412. The one or more batteries serve as a power source for the lamp provided within the fiber-illuminated handle 400. The optical pathway 412 supplies light, emitted from the lamp, to the light guide interface 339 of the fiber-illuminated blade 300 when the fiber-illuminated blade 300 is connected to the fiber-illuminated handle 400 in an operating position, described below.

The hook-on fitting 410 of the fiber-illuminated handle 400 is specifically designed for attachment to the blade fitting 330 of the fiber-illuminated blade 300, and vice versa. The hook-on fitting 410 includes an end of the optical pathway 412, first and second side supports 414a, 414b, and a hinge pin 418. The first and second side supports 414a, 414b extend vertically from the top of the grip 402. The first and second side supports 414a, 414b extend parallel to each other and are spaced apart from each other. The space bounded within the top of the grip 402 and the first and second side supports 414a, 414b forms a seat 419. The seat 419 has a width $W_F$ between the first and second side supports 414a, 414b. The width $W_F$ is greater than the thickness $T_F$ of the body 332 of the blade fitting 330 such that the seat 419 is configured to receive the body 332 of the blade fitting 330 therein.

The hinge pin 418 is attached to (i.e., extends through) the front of each of the first and second side supports 414a, 414b and extends across the seat 419. The hinge pin 418 is a cylinder having a diameter $d_F$. The diameter $d_F$ is less than the diameter of the semicircular bearing surface 335 of the blade fitting 330 of the fiber-illuminated blade 300 such that the hinge pin 418 is configured to be received within, and be rotatably supported by, the hinge slot 334. The hinge lock 336 is configured to lock the hinge pin 418 within the hinge slot 334.

The first and second side supports 414a, 414b respectively include first and second lock slots 416a, 416b that protrude into a seat-facing side of the respective side support (the second lock slot 416b is shown in FIG. 11C, discussed below). The first and second lock slots 416a, 416b are configured to receive a respective one of the first and second side locks 338a, 338b of the blade fitting 330 to hold the body 332 within the seat 419. The first and second lock slots 416a, 416b are each respectively positioned with respect to a center point of the hinge pin 418 to ensure that the first and second side locks 338a, 338b fit within respective ones of the first and second lock slots 416a, 416b when the fiber-illuminated blade 300 is engaged with the fiber-illuminated handle 400 in the operating position. As shown in FIG. 4C, a center of the first lock slot 416a is spaced from the center point of the hinge pin 418, designated at the intersection of the hinge pin crosshairs, by a distance having a horizontal distance component $D_{FLS\_h}$, and a vertical distance component $D_{FLS\_v}$. The center of the first lock slot 416a is spaced rearwardly from the center point of the hinge pin 418 by the horizontal distance component $D_{FLS\_h}$, and is spaced below the center point of the hinge pin 418 by the vertical distance component $D_{FLS\_v}$. A center point of the second lock slot 416b is provided at a corresponding position at the seat-facing side of the second side support 414b with respect to the center point of the hinge pin 418 such that the first and second lock slots 416a, 416b are spaced the same distance from the center of the hinge pin 418.

The blade fitting 330 of the fiber-illuminated blade 300 is configured to engage with hook-on fitting 410 of the fiber-illuminated handle 400 to lock the fiber-illuminated blade 300 within the fiber-illuminated handle 400 in an operating position, in which the laryngoscope is ready-for-use. To place the fiber-illuminated blade 300 in the operating position, the blade fitting 330 is first attached to the hook-on fitting 410. The blade fitting 330 is attached to the hook-on fitting 410 of the fiber-illuminated handle 400 by placing the hinge pin 418 of the hook-on fitting 410 within the hinge slot 334 of the blade fitting 330 and providing relative movement between the hinge pin 418 and the hinge slot 334 until the hinge pin 418 abuts against the semicircular bearing surface 335 of the hinge slot 334 and is locked therein by the hinge lock 336. Relative rotational movement is provided between the fiber-illuminated blade 300 and the fiber-illuminated handle 400 such that the hinge slot 334 and the hinge pin 418 are rotated relative to one and other until the body 332 of the blade fitting 330 slides within the seat 419 of the hook-on fitting 410. When the body 332 of the blade fitting 330 is fully received within the seat 419 of the hook-on fitting 410, the first and second side locks 338a, 338b of the blade fitting 330 respectively engage with the first and second lock slots 416a, 416b of the hook-on fitting 410. The fiber-illuminated blade 300 is thus locked within the fiber-illuminated handle 400 in the operating position. In the operating position, the light guide interface 339 of the blade fitting 330 is engaged with the optical pathway 412 of the hook-on fitting 410, and the laryngoscope is ready-for-use.

Critical dimensions of conventional blades, conventional handles, fiber-illuminated blades, and fiber-illuminated handles conform to International Organization for Standardization (i.e., ISO)—International Standard 7376 for "Anesthetic and respiratory equipment—Laryngoscopes for tracheal intubation," which provides general requirements for laryngoscopes used for intubation. Because of the fitting standardization provided by ISO Standard 7376, conventional blades of varying types and sizes are interchangeably connectable with conventional handles of varying sizes and shapes. Similarly, fiber-illuminated blades of varying types and sizes are interchangeably connectable with fiber-illuminated handles of varying types and sizes.

With known interchangeable laryngoscope blades and handles, conventional blades will not function with fiber-illuminated handles, since fiber-illuminated handles do not include electrical contacts to supply the lamp of the conventional blade with power from batteries disposed within the handle. Similarly, fiber-illuminated blades will not function with conventional handles, since conventional handles include neither the lamp nor the optical pathway for interfacing with the light guide of the fiber-illuminated blade.

Accordingly, the dimensions of the blade fittings and hook-on fittings prescribed by ISO Standard 7376 intentionally limits the mechanical interchangeability of laryngoscope blades and handles to prevent handle/blade engagement that will not properly function (e.g., that will not produce light to illuminate the larynx). That is, blade fittings of conventional blades dimensioned to ISO Standard 7376 will not engage with hook-on fittings of fiber-illuminated handles dimensioned to ISO Standard 7376 for fiber-illuminated handles, and blade fittings of fiber-illuminated blades dimensioned to ISO Standard 7376 will not engage with hook-on fittings of conventional handles dimensioned to ISO Standard 7376 for conventional handles. For example, the thickness $T_C$ of the body 132 of the conventional blade 100 is less than the thickness $T_F$ of the body 332 of the fiber-illuminated blade 300, and the width $W_C$ of the seat 219 of the conventional handle 200 is less than the width $W_F$ of the seat 419 of the fiber-illuminated handle 400. Due to this configuration, engagement between the blade fitting 330 of the fiber-illuminated blade 300 and the hook-on fitting 210 of the conventional handle 200 is prevented because the thickness $T_F$ of the body 332 of the fiber-illuminated blade 300 is thicker than the width $W_C$ of the seat 219 of the conventional handle 200. That is, the body 332 of the fiber-illuminated blade 300 is too thick to fit within the seat 219 of the conventional handle 200.

Further, the diameter of the semicircular bearing surface 135 of the hinge slot 134 of the conventional blade 100 is smaller than the diameter of the semicircular bearing surface 335 of the hinge slot 334 of the fiber-illuminated blade 300, and the diameter $d_C$ of the hinge pin 218 of the conventional handle 200 is smaller than the diameter $d_F$ of the hinge pin 418 of the fiber-illuminated handle 400. Due to this configuration, engagement between the blade fitting 130 of the conventional blade 100 and the hook-on fitting 410 of the fiber-illuminated handle 400 is prevented because the diameter $d_F$ of the hinge pin 418 of the fiber-illuminated handle 400 is too large to fit properly within the semicircular bearing surface 135 of the hinge slot 134 of the conventional blade 100.

The limited interchangeability of laryngoscope blades and handles renders obsolete otherwise useful laryngoscope handles that do not interface with incompatible laryngoscope blades. The limited interchangeability can limit a users' choice of laryngoscope blades. For example, if an institution (e.g., a hospital) makes a significant investment in fiber-illuminated laryngoscope blades and handles, it is costly to later switch to conventional blades because doing so would render obsolete the stock of otherwise useful fiber-illuminated handles that are not connectable with the conventional blades.

SUMMARY

The present inventors recognize that there exists a need for a universal laryngoscope blade that addresses the shortcomings of current laryngoscope blades. There exists a need for a universal laryngoscope blade that is interchangeably connectable to, and functional with, hook-on fittings of both conventional handles and fiber-illuminated handles that are dimensioned according to ISO Standard 7376.

According to one aspect of the invention, a universal laryngoscope blade comprises a blade body shaped to provide a direct view of a larynx. The blade body includes a first end and a second end. The second end is configured for insertion into the larynx. The universal laryngoscope blade further comprises a viewer connected to the blade body. The viewer being configured to function independently from each of a conventional handle and a fiber-illuminated handle. The universal laryngoscope blade further comprises a blade fitting disposed at the first end of the blade body. The blade fitting is removably connectable to, one at a time, each of a hook-on fitting of the conventional handle and a hook-on fitting of the fiber-illuminated handle. The hook-on fitting of the conventional handle having at least one physical dimension that is different from at least one physical dimension of the hook-on fitting of the fiber-illuminated handle.

According to another aspect of the invention, the universal laryngoscope blade may further comprise a power source configured to be in electrical communication with the viewer to supply power to the viewer when the laryngoscope blade is engaged to one of the conventional handle and the fiber-illuminated handle in an operating position. The blade fitting may include a first electrical contact in electrical communication with the power source and a second electrical contact in electrical communication with the viewer, wherein the first electrical contact is configured to be in electrical communication with the second electrical contact via a hinge pin of one of the conventional handle and the fiber-illuminated handle when the laryngoscope blade is in the operating position. The first electrical contact may be in electrical communication with the power source via a first electrical wire, and the second electrical contact may be in electrical communication with the viewer via a second electrical wire.

According to another aspect of the invention, a method of engaging universal laryngoscope blades with a conventional handle and a fiber-illuminated handle comprises providing a first universal laryngoscope blade of the universal laryngoscope blades. The first universal laryngoscope blade comprises a blade body including a first end and a second end. The first universal laryngoscope blade further comprises a viewer connected to the blade body. The viewer is configured to function independently from each of the conventional handle and the fiber-illuminated handle. The first universal laryngoscope blade further comprises a blade fitting disposed at the first end of the blade body. The method further comprises providing a second universal laryngoscope blade of the universal laryngoscope blades. The second universal laryngoscope blade comprises a blade body including a first end and a second end. The second universal laryngoscope blade further comprises a viewer connected to the blade body. The viewer is configured to function independently from each of the conventional handle and the fiber-illuminated handle. The second universal laryngoscope blade further comprises a blade fitting disposed at the first end of the blade body. The blade fitting of the first universal laryngoscope blade and the blade fitting of the second universal laryngoscope blade being identically dimensioned. The method further comprises providing the conventional handle. The conventional handle including a hook-on fitting comprising a seat having a width and a hinge pin having a diameter. The method further comprises providing the fiber-illuminated handle. The fiber-illuminated handle including a hook-on fitting comprising a seat having a width and a hinge pin having a diameter. The width of the seat of the fiber-illuminated handle is greater than the width of the seat of the conventional handle, the diameter of the hinge pin of the fiber-illuminated handle is greater than the diameter of the hinge pin of the conventional handle. The method further comprises engaging the blade fitting of the first universal laryngoscope blade with the hook-on fitting of the conventional handle such that the first universal laryngoscope blade is provided in an operating position and ready-for-use. The method further comprises engaging the blade fitting of the second universal laryngoscope blade with the hook-on fitting of the fiber-illuminated handle such that the second universal laryngoscope blade is provided in an operating position and ready-for-use.

There are, of course, additional aspects of the various embodiments of the invention disclosed herein that will be described below and which will form the subject matter of the claims. In this respect, before explaining at least one aspect of the invention in detail, it is to be understood that the invention is not limited in its application to the details of construction and to the arrangements of the components set forth in the following description or illustrated in the drawings. The invention is capable of aspects in addition to those described and of being practiced and carried out in various ways. Also, it is to be understood that the phraseology and terminology employed herein, as well as the Abstract, are for description and should not be regarded as limiting.

As such, those skilled in the art will appreciate that the conception upon which this invention is based may readily be utilized as a basis for the designing of other structures, methods, and systems for carrying out the several purposes of the invention. It is important, therefore, that the claims be regarded as including such equivalent constructions insofar as they do not depart from the spirit and scope of the invention.

BRIEF DESCRIPTION OF DRAWINGS

In order that the invention may be readily understood, aspects of the invention are illustrated by way of examples in the accompanying drawings; however, the subject matter is not limited to the disclosed aspects.

FIG. 3A shows a side view of a known fiber-illuminated blade.

FIG. 3B shows a rear view of the known fiber-illuminated blade.

FIG. 3C shows a magnified side view of the blade fitting of the known fiber-illuminated blade.

FIG. 9A shows a rear view of the universal laryngoscope blade engaged with the conventional handle in the operating position in accordance with aspects of the invention.

FIG. 9B shows a magnified cross-sectional view of the engagement between blade fitting of the universal laryngoscope blade and the hook-on fitting of the conventional handle of FIG. 9A taken along section F-F.

FIG. 9C shows a magnified cross-sectional view of the engagement between the blade fitting of the universal laryngoscope blade and the hook-on fitting of the conventional handle of FIG. 9A taken along section H-H.

Features of the universal laryngoscope blade and associated methods according to aspects of the invention are described with reference to the drawings, in which like reference numerals refer to like parts throughout.

DETAILED DESCRIPTION

Figure 1A:
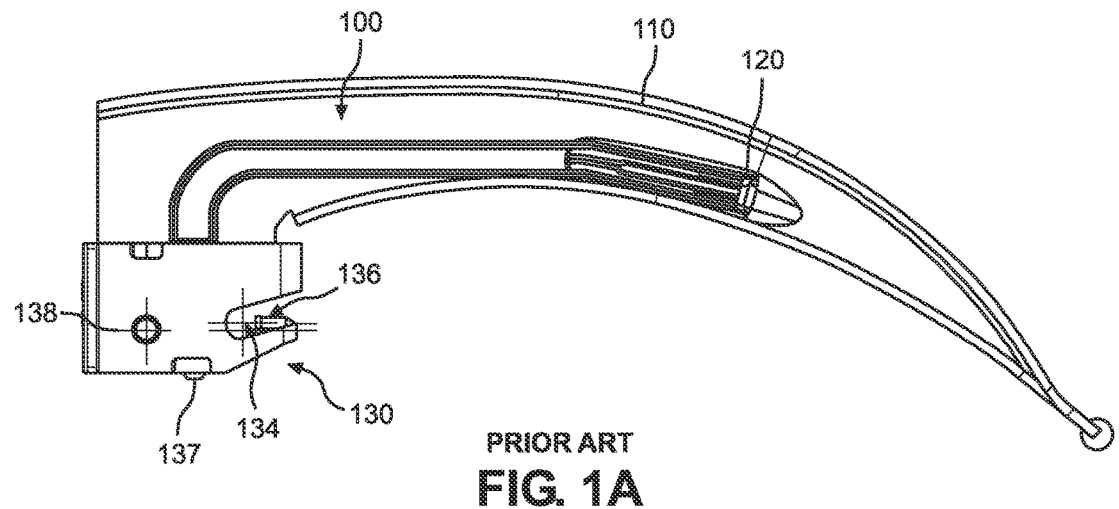
FIG. 1A shows a side view of a known conventional blade.
Figure 1B:
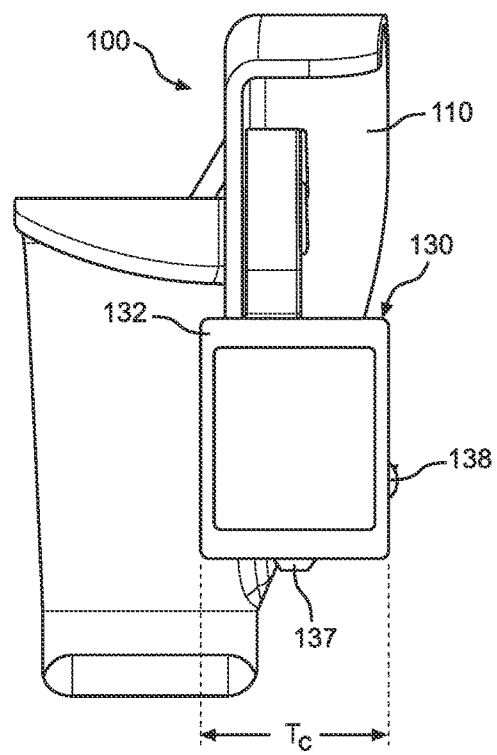
FIG. 1B shows a rear view of the known convention blade.
Figure 1C:
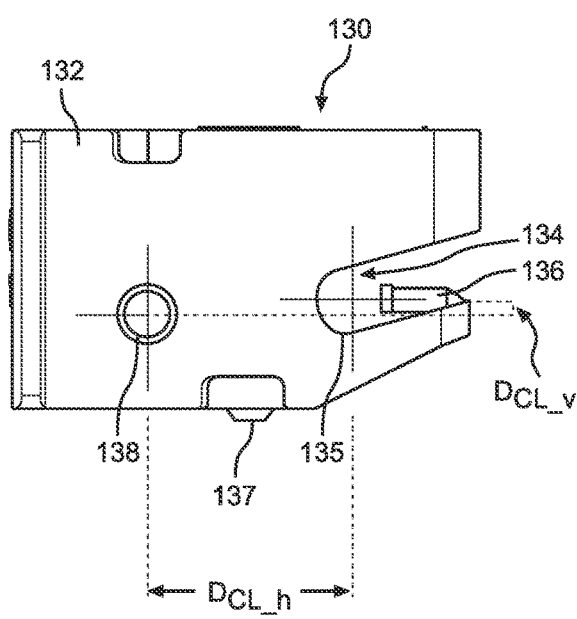
FIG. 1C shows a magnified side view of the blade fitting of the known conventional blade.
Figure 2A:
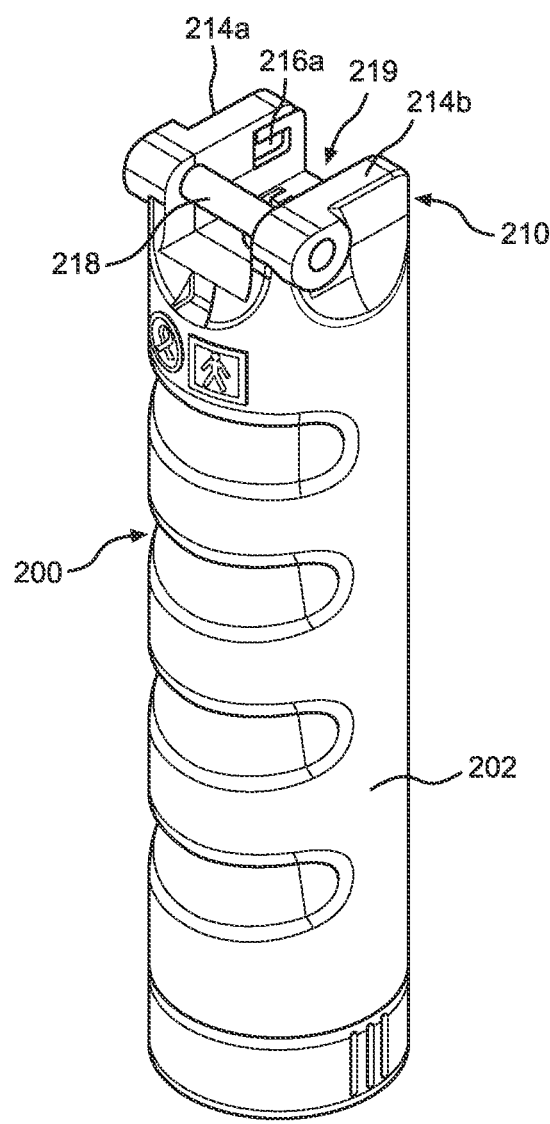
FIG. 2A shows a perspective view of a known conventional handle.
Figure 2B:
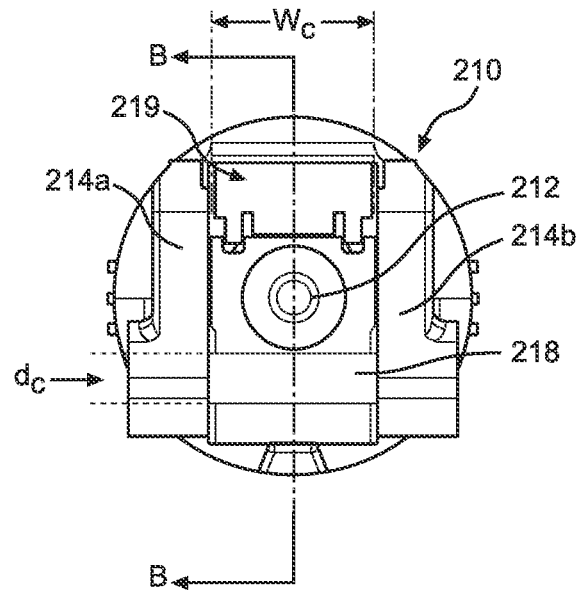
FIG. 2B shows a top view of a hook-on fitting of the known conventional handle.
Figure 2C:
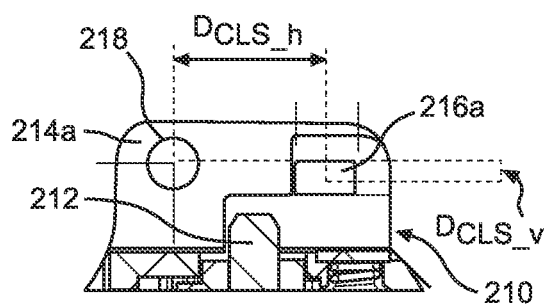
FIG. 2C shows a cut-away side view of the hook-on fitting of the known conventional handle taken along section B-B of FIG. 2B.
Figure 4A:
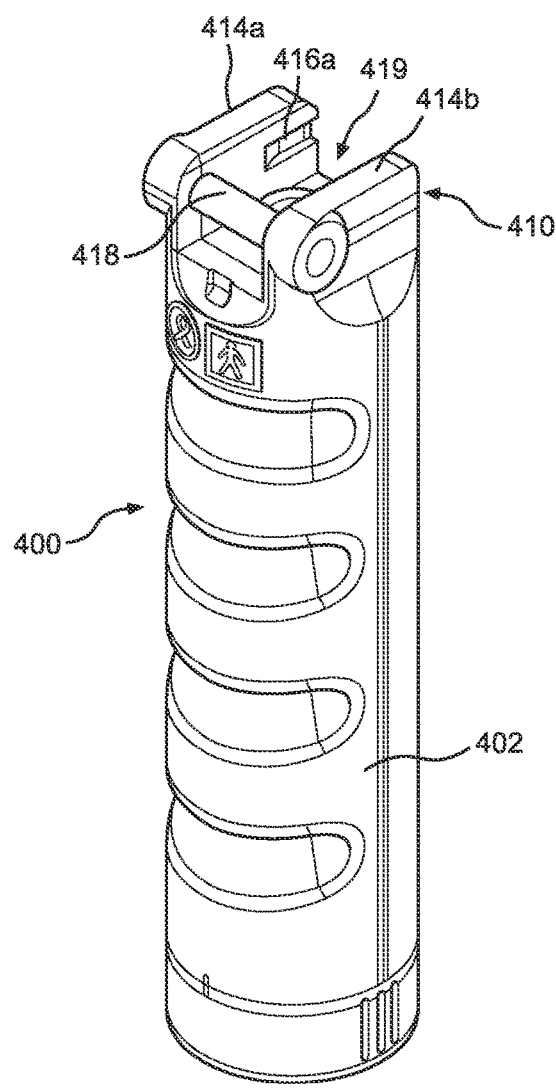
FIG. 4A shows a perspective view of a known fiber-illuminated handle.
Figure 4B:
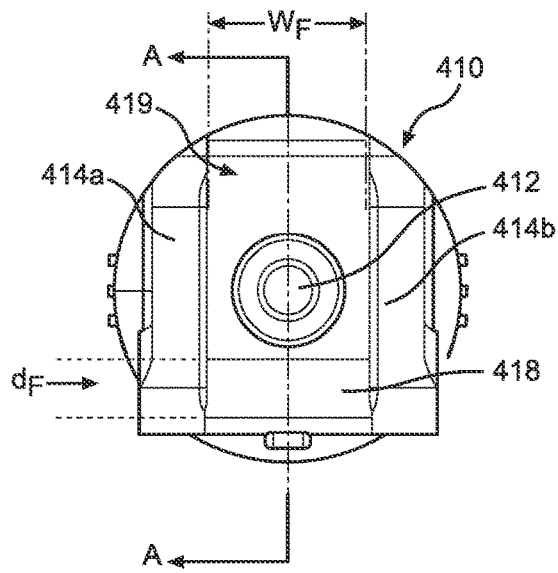
FIG. 4B shows a top view of the hook-on fitting of the known fiber-illuminated handle.
Figure 4C:
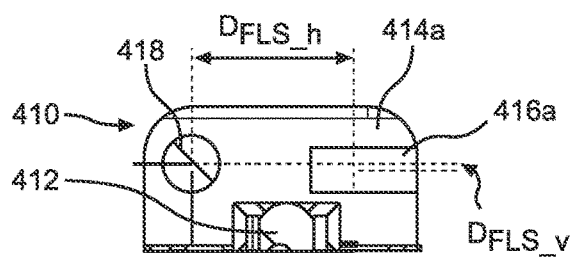
FIG. 4C shows a cut-away side view of the hook-on fitting of the known fiber-illuminated handle taken along section A-A of FIG. 4B.
Figure 5A:
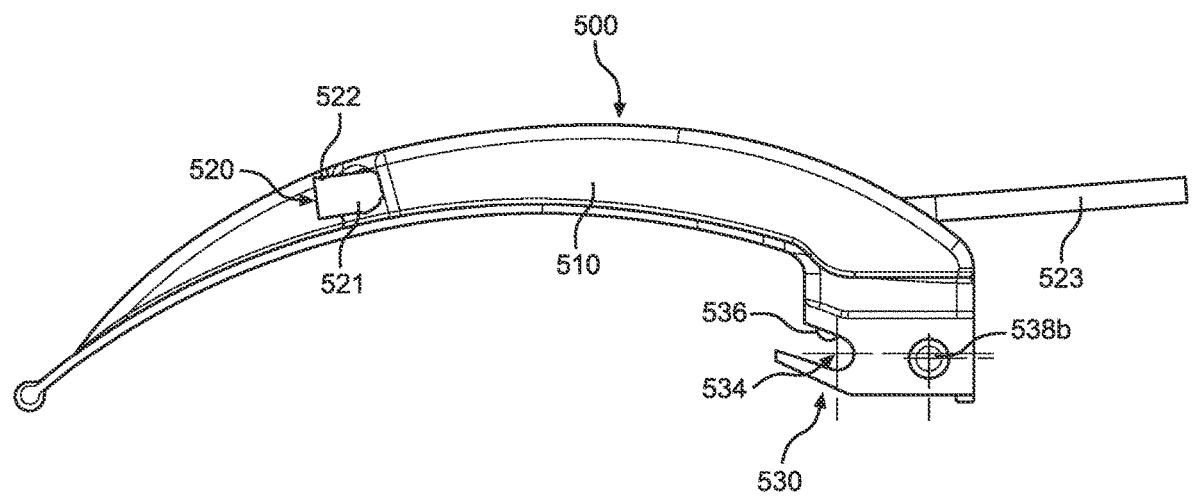
FIG. 5A shows a side view of an exemplary universal laryngoscope blade having at least one cable for direct connection to an external device in accordance with aspects of the invention.
Figure 5B:
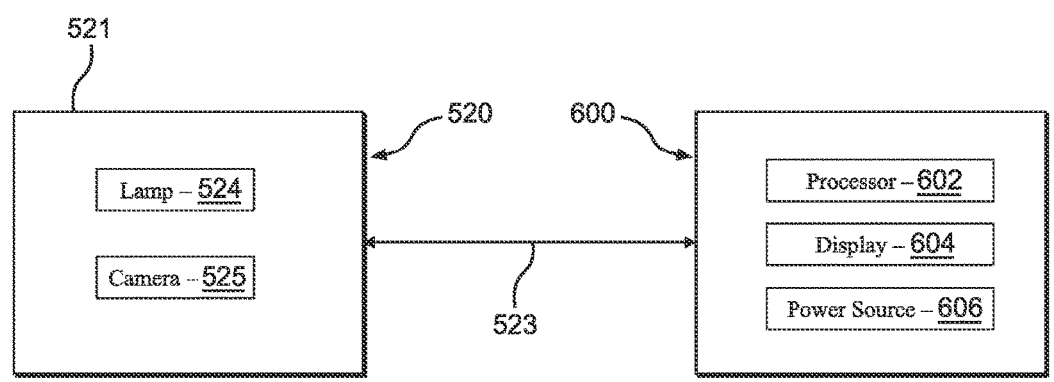
FIG. 5B shows a schematic representation of an exemplary embodiment of a viewer of the universal laryngoscope and of an external device in accordance with aspects of the invention.
Figure 6A:
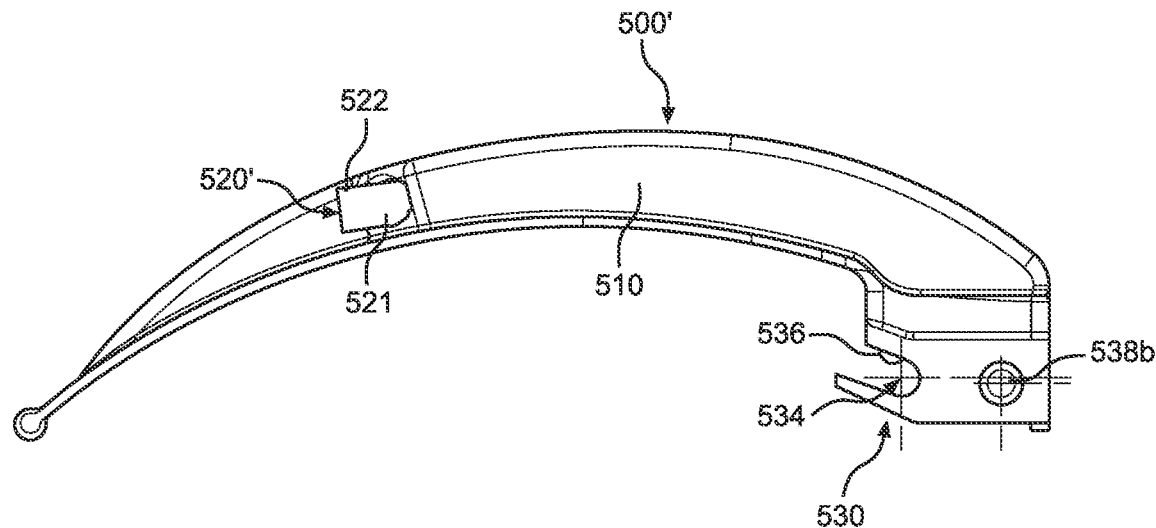
FIG. 6A shows a side view of another exemplary universal laryngoscope blade embodiment having a viewer without any direct connection to an external device in accordance with aspects of the invention.
Figure 6B:
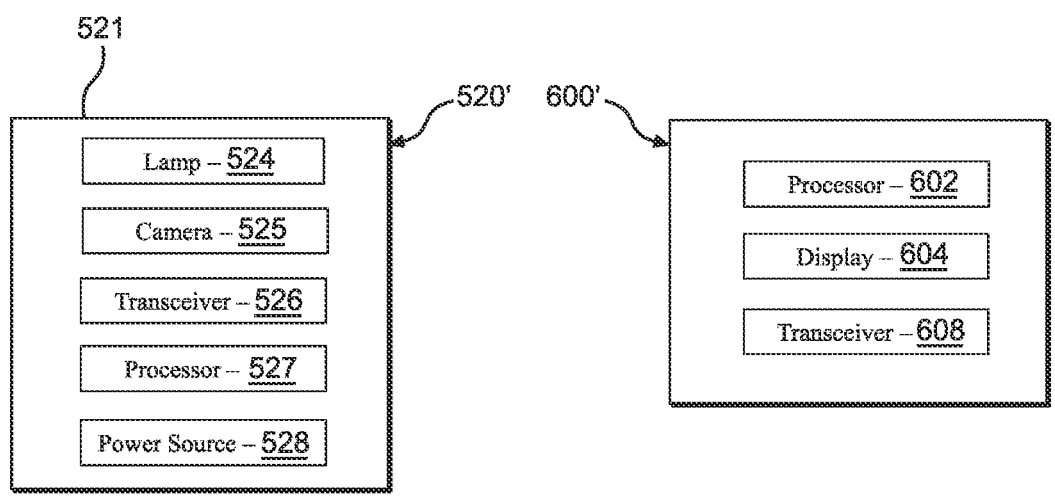
FIG. 6B shows a schematic representation of another exemplary embodiment of the viewer of the universal laryngoscope and of the external device in accordance with aspects of the invention.
Figure 7A:
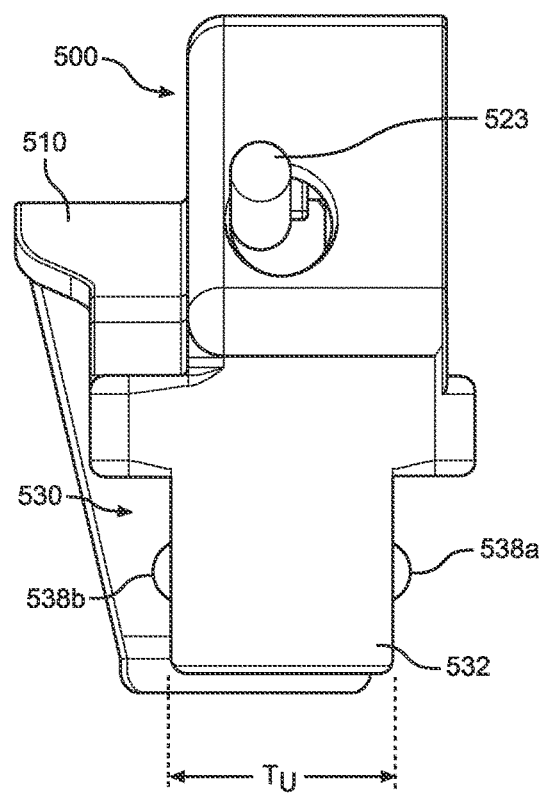
FIG. 7A shows a magnified rear view of a blade fitting in accordance with aspects of the invention.
Figure 7B:
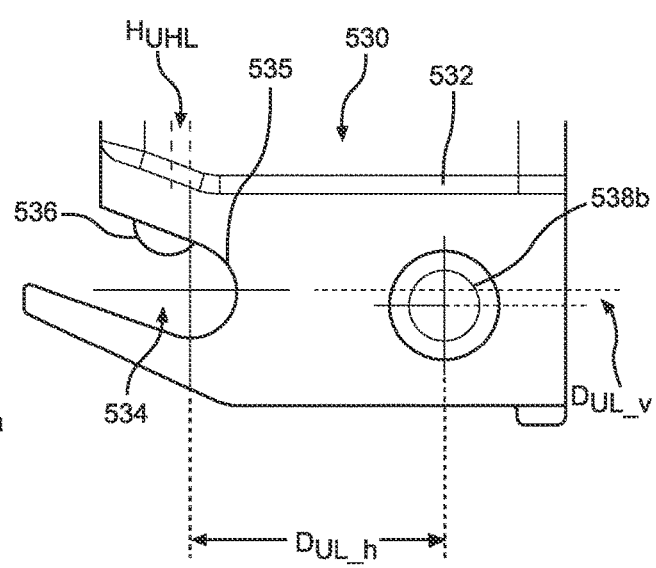
FIG. 7B shows a magnified side view of the blade fitting in accordance with aspects of the invention.

FIGS. 5A-7B show exemplary views of universal laryngoscope blades in accordance with aspects of the invention. FIG. 5A shows a side view of an exemplary universal laryngoscope blade 500 having at least one cable 523 for direct connection to an external device 600. FIG. 5B shows a schematic representation of an exemplary embodiment of the viewer 520 and the external device 600. FIG. 6A shows a side view of another exemplary universal laryngoscope blade 500' having a viewer 520' without any direct connection to an external device 600'. FIG. 6B shows a schematic representation of another exemplary embodiment of the viewer 520' and the external device 600'. FIG. 7A shows a magnified rear view of the blade fitting 530 in accordance with aspects of the invention. FIG. 7B shows a magnified side view of the blade fitting 530 in accordance with aspects of the invention.

The universal laryngoscope blade 500 includes a blade body 510, a viewer 520, and a blade fitting 530. The universal laryngoscope blade 500 may be, entirely or partially, reusable or disposable. The blade body 510 may be shaped to provide a direct view of a larynx. The blade body 510 may be provided in any number of shapes and sizes depending, e.g., on the size of the patient, as would be readily understood by a person having ordinary skill in the art. The blade body 510 may include a first end and a second end. The second end may be inserted into the larynx of a patient.

The viewer 520 is connected to the blade body 510 and may illuminate the larynx when the second end of the blade body 510 is inserted therein. The viewer 520 may function (e.g., emit light, capture at least one image, etc.) independently from each of the conventional handle 200 and the fiber-illuminated handle 400. That is, the viewer 520 does not rely on a laryngoscope handle for power, signal transmission, light emission, etc. The viewer 520 may include a housing 521. The housing 521 may be provided within a chamber of the blade body 510. Additionally, or alternatively, the housing 521 may be attached to an outer side of the blade body 510. The housing 521 may include an opening 522, positioned between the second end of the blade body 510 and the central portion of the blade body 510. The opening 522 may open towards the second end of the blade body 510. The opening 522 may be covered with a transparent window to seal an interior of the housing 521. The transparent window may include a lens. The viewer 520 may include one or more cables 523. The one or more cables 523 may define the housing 521. The one or more cables 523 may extend from a rear of the blade body 510 for connection to an external device 600. The external device 600 may be a device other than a laryngoscope handle. The external device 600 may include one or more of, e.g., a processor 602, a display 604, a power source 606, a lamp, a transceiver 608 (the term "transceiver" as used herein includes one or more of each of a transmitter and a receiver combined into a single circuitry, or provided separately, capable of transmitting and receiving electronic signals), etc. The one or more cables 523 may be capable of transmitting light, electricity, data, etc., between the viewer 520 and the external device 600.

The viewer 520 may include a lamp 524 that emits light from the opening 522 of the housing 521 in a direction towards the second end of the blade body 510 to illuminate the second end of the blade body 510 and/or the larynx. The lamp 524 may be provided within the housing 521. The lamp 524 may be hermetically sealed within the housing 521. Alternatively, the external device 600 may include the lamp 524, and light may be directed through the one or more cables 523 to the opening 522 to illuminate the second end of the blade body 510 and/or the larynx.

The viewer 520 may include a camera 525 that may capture one or more images, from the perspective of the opening 522 of the housing 521, of the second end of the blade body 510 and/or of the larynx. At least a portion of the camera 525, and in embodiments the entire camera 525, may be provided within the housing 521. The camera 525 may be hermetically sealed within the housing 521. Images collected by the camera 525 may be electronically transferred to the external device 600. For example, the images may be electronically transferred via the one or more cables 523. Additionally, or alternatively, the viewer 520 may include a transceiver 526 that may wirelessly transmit the images to the external device 600. The transceiver 526 may receive control instructions from the processor 602. The viewer 520 may also include a processor 527 that may control any of the lamp 524, camera 525, transceiver 526, etc. The processor 527 may independently control the lamp 524, camera 525, and/or transceiver 526, or may be used to implement control instructions transmitted from the external device 600 and received by the transceiver 526.

The viewer 520 may include a power source 528 (e.g., a battery) that supplies power to the lamp 524, camera 525, transceiver 526, processor 527, etc. The power source 528 may be provided on the blade body 510. The powers source 528 may be positioned within, or connected to, the housing 521. Additionally, or alternatively, power may be supplied to the lamp 524 and/or the camera 525 from the external device 600 via the one or more cables 523.

As shown in FIGS. 5A and 5B, according to an embodiment of the invention, the viewer 520 may include the one more cables 523 that may supply light, electricity, and/or data. The viewer 520 may also include the lamp 524, and optionally the camera 525. The external device 600 may include a processor 602, a display 604, and a power source 606. The one or more cables 523 provide electronic communication between, e.g., the external device 600, and the lamp 524 and the camera 525. For example, the one or more cables 523 transmit power to the lamp 524 and to the camera 525. Images captured by the camera 525 are transmitted to the external device 600 via the one or more cables 523. The processor 602 may control the lamp 524 and the camera 525 via signals sent through the at one or more cables 523.

As shown in FIGS. 6A and 6B, according to another embodiment of the invention, the viewer 520' may be provided without any direct connection (i.e., cable link) with the external device 600'. For example, the viewer 520' may include the lamp 524, and optionally the camera 525. The viewer 520' also may include a power source 528 (e.g., a battery), a transceiver 526, and a processor 527. The external device 600' may include a processor 602, a display 604, and a transceiver 608. According to aspects invention, the viewer 520' is fully functional (i.e., capable of producing/transmitting light/data, capable of capturing one or more images, etc.) without the need for the blade fitting 530 to interface with functional elements (e.g., the electrical contact 212 of the conventional handle 200 or the optical pathway 412 of the fiber-illuminated handle 400) on the conventional handle 200 or the fiber-illuminated handle 400. In other words, the viewer 520' is self-contained in that it may draw power form a source (e.g., an internal power source 528) other than the handle.

The blade fitting 530 is disposed at the first end of the blade body 510. As discussed above, the hook-on fitting 210 of the conventional handle 200 has at least one physical dimension (e.g., the diameter $d_C$ of the hinge pin 218, the width We of the seat 219, etc.) that is different from at least one physical dimension (e.g., the diameter $d_F$ of the hinge pin 418, the width $W_F$ of the seat 419) of the hook on fitting of the fiber-illuminated blade 300. Further, the hook-on fitting 210 of the conventional handle 200 is dimensioned to conform to ISO standard 7376 for conventional handles and the hook-on fitting 410 of the fiber-illuminated handle 400 is dimensioned to conform to ISO standard 7376 for fiber-illuminated handles. Nevertheless, the blade fitting 530 of the present invention is removably connectable to, and functional with, each of the hook-on fitting 210 of the conventional handle 200 and the hook-on fitting 410 of the fiber-illuminated handle 400. The blade fitting 530 of the invention may also be adapted for removable connection to, and functionality with, hook-on fittings of other handles that differ from the hook-on fitting 210 of the conventional handle 200 and the hook-on fitting 410 of the fiber-illuminated handle 400 described herein.

The blade fitting 530 of the universal laryngoscope blade 500 includes a body 532, a lock, and a hinge slot 534. As shown in FIG. 7A, the body 532 has a thickness $T_U$. The thickness $T_U$ of the body 532 of the universal laryngoscope blade 500 may be greater than the thickness $T_C$ of the body of the conventional blade 100 but less than the thickness $T_F$ of the body 332 of the fiber-illuminated blade 300. For example, the thickness $T_U$ may be between 12.74 and 12.84 mm, and more particularly may be 12.80 mm. According to aspects of the invention, because the thickness $T_U$ of the body 532 of the universal laryngoscope blade 500 may be greater than the thickness $T_C$ of the body 132 of the conventional blade 100 but less than the thickness $T_F$ of the body 332 of the fiber-illuminated blade 300, the body 532 of the universal laryngoscope blade 500 may be small enough to be received within the seat 219 of the conventional handle 200 while large enough to limit excessive play (wobbling) when received within the seat 419 of the fiber-illuminated handle 400. That is, the body 532 of the universal laryngoscope blade 500 may be accommodated within, one at a time, the seat 219 of the conventional handle 200 and the fiber-illuminated handle 400, improving the universality of blade fitting 530 of the universal laryngoscope blade 500. A bottom of the body 532 may not include (i.e., may be free of) functional elements (e.g., electrical contacts, light guides, etc.) that would otherwise protrude from the body 532. By not including functional elements on the body 532 of the blade fitting 530, the bottom of the body 532 of the blade fitting 530 may not interfere with functional elements (e.g., electrical contacts, optical pathways, etc.) provided on the hook-on fittings of conventional handles and/or fiber-illuminated handles when connected thereto. Alternatively, the bottom of the body 532 may be equipped with a switch that activates the viewer 520 when the universal laryngoscope blade 500 is engaged with the conventional handle 200/the fiber-illuminated handle 400 in the operating position.

The lock may include a hinge lock 536 disposed within a top surface of the hinge slot 534. In embodiments, the hinge lock 536 may be disposed within a bottom surface of the hinge slot 534. The lock may also include at least one side lock provided on at least one side of the body 532. As is shown in FIG. 7A, the at least one side lock may include first and second side locks 538a, 538b respectively provided on opposite sides of the body 532. A center point of the second side lock 538b is indicted at the intersection of side lock crosshairs, as shown in FIG. 7B. The hinge lock 536, the first side lock 538a, and/or the second side lock 538b may be detent mechanisms. The hinge slot 534 may extend into the body 532 at an angle from a front of the body 532 towards a central region of the body 532 and may terminate at a bearing surface 535. The bearing surface 535 has semicircular shape having a diameter and a virtual center point, indicated by the intersection of hinge slot 534 crosshairs shown in FIG. 7B, about which the bearing surface 535 forms the semicircular shape. The diameter of the semicircular bearing surface 535 of the hinge slot 534, and a width of the hinge slot 534 in general, are dimensioned to accommodate, one at a time, the hinge pin 218 of the conventional handle 200 and the hinge pin 418 of the fiber-illuminated handle 400 such that the respective hinge pin is received within and abuts against the semicircular bearing surface 535. That is, the hinge slot 534 is dimensioned to receive in abutment with the semicircular bearing surface 535, one at a time, the hinge pin 218 of the hook-on fitting 210 of the conventional handle 200 and the hinge pin 418 of hook-on fitting 410 of the fiber-illuminated handle 400. For example, the diameter of the semicircular bearing surface 535 of the hinge slot 534, and a narrowest width of the hinge slot 534 in general, are each at least greater than 4.58 mm.

As shown in FIG. 7B, a center of the hinge lock 536 is spaced forwardly from the virtual center of the semicircular bearing surface 535 by a horizontal distance $H_{UHL}$. The horizontal distance $H_{UHL}$ that the hinge lock 536 of the universal laryngoscope blade 500 is spaced forwardly from the virtual center of the semicircular bearing surface 535 of the universal laryngoscope blade 500 is less than the horizontal distance $H_{FHL}$ that the hinge lock 336 of the fiber-illuminated blade 300 is spaced forwardly from the virtual center of the semicircular bearing surface 335 of the fiber-illuminated blade 300. For example, the horizontal distance HURL that the hinge lock 536 of the universal laryngoscope blade 500 is spaced forwardly from the virtual center of the semicircular bearing surface 535 of the universal laryngoscope blade 500 may be between 0.86 and 0.90 mm, and more particularly may be 0.88 mm. By locating the hinge lock 536 the horizontal distance $H_{UHL}$ forwardly from the virtual center of the semicircular bearing surface 535, the hinge lock 536 may securely hold, one at a time, the hinge pin 218 of the conventional handle 200 and the hinge pin 418 of the fiber-illuminated handle 400 within the hinge slot 534 of the blade fitting 530. That is, the hinge slot 534 and the hinge lock 536 of the universal laryngoscope blade 500 may accommodate, one at a time, the hinge pin 218 of the conventional handle 200, and the larger hinge pin 418 of the fiber-illuminated handle 400, improving the universality of the blade fitting 530 of the universal laryngoscope blade 500.

The center point of the second side lock 538b may be spaced from the virtual center point of the semicircular bearing surface 535 by a distance having a horizontal distance component $D_{UL\_h}$, and a vertical distance component $D_{UL\_v}$. The center point of the second side lock 538b may be spaced rearwardly from the virtual center point of the semicircular bearing surface 535 by the horizontal distance component $D_{UL\_h}$, and may be spaced below the virtual center point of the bearing surface 535 by the vertical distance component $D_{UL\_v}$. A center point of the first side lock 538a may be provided at a corresponding position at the other side surface of the body 532 with respect to the virtual center point of the semicircular bearing surface 535 such that the first and second side locks 538a, 538b are spaced the same distance from the virtual center point of the semicircular bearing surface 535.

The horizontal distance component $D_{UL\_h}$, and the vertical distance component $D_{UL\_v}$ may be set such that the side lock (i.e., the first side lock 538a or the second side lock 538b) may be accommodated within a respective lock slot of the conventional handle 200 when the universal laryngoscope blade 500 is engaged with the hook-on fitting 210 of the conventional handle 200 in an operating position, in which the laryngoscope is ready-for-use. The horizontal distance component $D_{UL\_h}$, and the vertical distance component $D_{UL\_v}$ may be set such that the side lock (i.e., the first side lock 538a or the second side lock 538b) may also be accommodated within a respective lock slot of the fiber-illuminated handle 400 when the universal laryngoscope blade 500 is engaged with the hook-on fitting 410 of the fiber-illuminated handle 400 in the operating position. For example, the horizontal distance component $D_{UL\_h}$ may be of a magnitude greater than the horizontal distance component $D_{CL\_h}$ of the blade fitting 130 of the conventional blade 100 and less than the horizontal distance component $D_{FLh}$ of the blade fitting 330 of the fiber-illuminated blade 300. The horizontal distance component $D_{UL\_h}$ may be 13.0 mm. The vertical distance component $D_{UL\_v}$ may be 0.8 mm.

As a result of the above-described features and dimensions (e.g., the thickness $T_U$ of the body 532, the width of the hinge slot 534, the diameter of the semicircular bearing surface 535 of the hinge slot 534, the horizontal distance $H_{UHL}$, the horizontal distance component $D_{UL\_h}$, the vertical distance component $D_{UL\_v}$, etc.), the blade fitting 530 of the universal laryngoscope blade 500 may engage with, one at a time, both the hook-on fitting 210 of the conventional handle 200 and the hook-on fitting 410 of the fiber-illuminated handle 400. Further, and as discussed above, the viewer 520 (or the viewer 520') is fully functional (i.e., capable of producing/transmitting light/data, capable of capturing one or more images, etc.) without the need for the blade fitting 530 to interface with functional elements (e.g., the electrical contact 212 of the conventional handle 200 or the optical pathway 412 of the fiber-illuminated handle 400) on the conventional handle 200 or the fiber-illuminated handle 400. Accordingly, the universal laryngoscope blade 500 may be attached to, and fully functional with, each of the conventional handle 200 and the fiber-illuminated handle 400 that are dimensioned to conform to the requirements of ISO Standard 7376. This may allow a user to remove handle compatibility from laryngoscope blade purchasing decisions to leverage initial investments in otherwise useful conventional handles and/or fiber-illuminated handles. Universal laryngoscope blades may also reap the benefits of economies of scale, since the universal laryngoscope blades may be produced in greater numbers due to the compatibility with both existing conventional handles and fiber-illuminated handles.

Figure 8A:
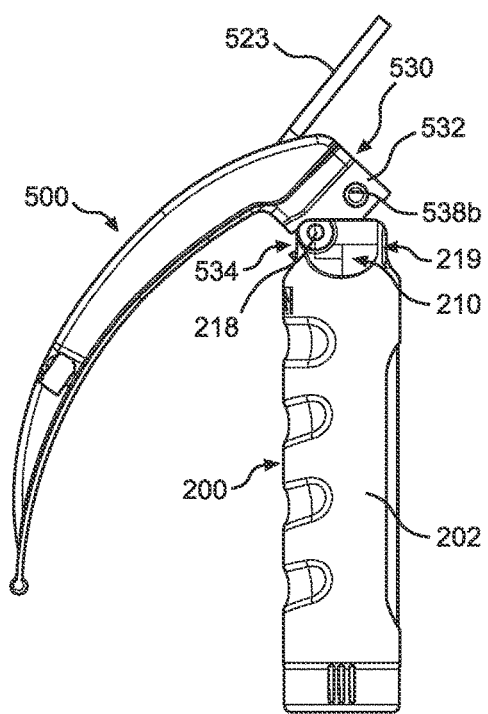
FIG. 8A shows a side view of the universal laryngoscope blade hooked-on to the hinge pin of the conventional handle in accordance with aspects of the invention.
Figure 8B:
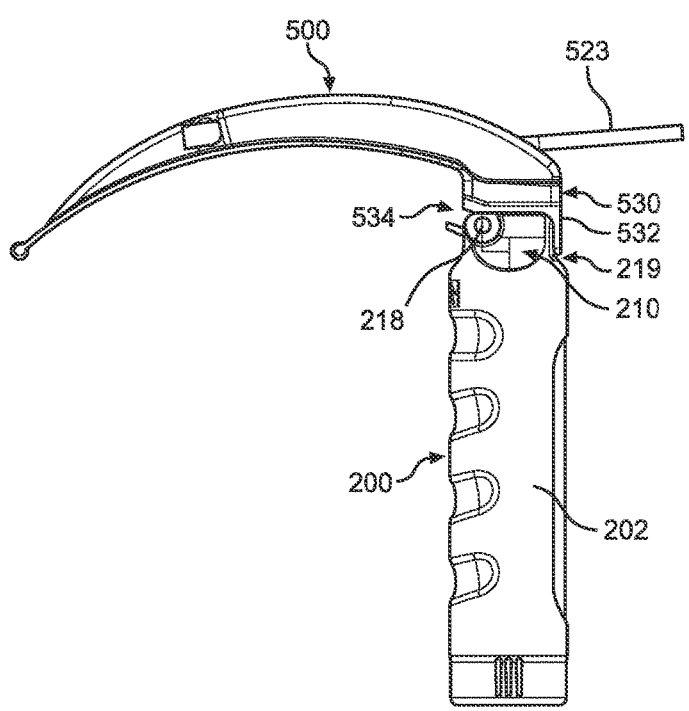
FIG. 8B shows a side view of the universal laryngoscope blade engaged with the conventional handle in the operating position in accordance with aspects of the invention.

FIGS. 8A-9C depict engagement of the universal laryngoscope blade 500 and the conventional handle 200. FIG. 8A shows a side view of the universal laryngoscope blade 500 hooked-on to the hinge pin 218 of the conventional handle 200. FIG. 8B shows a side view of the universal laryngoscope blade 500 engaged with the conventional handle 200 in the operating position. FIG. 9A shows a rear view of the universal laryngoscope blade 500 engaged with the conventional handle 200 in the operating position. FIG. 9B shows a magnified cross-sectional view of the engagement between blade fitting 530 of the universal laryngoscope blade 500 and the hook-on fitting 210 of the conventional handle 200 of FIG. 9A taken along section F-F. FIG. 9C shows a magnified cross-sectional view of the engagement between the blade fitting 530 of the universal laryngoscope blade 500 and the hook-on fitting 210 of the conventional handle 200 of FIG. 9A taken along section H-H.

The blade fitting 530 of the universal laryngoscope blade 500 is configured to engage with the hook-on fitting 210 of the conventional handle 200 to lock the universal laryngoscope blade 500 within the seat 219 of the conventional handle 200 in an operating position, in which the laryngoscope is ready-for-use. As shown in FIG. 8A, to place the universal laryngoscope blade 500 in the operating position, the blade fitting 530 is first attached to the hook-on fitting 210. The blade fitting 530 is attached to the hook-on fitting 210 of the conventional handle 200 by placing the hinge pin 218 of the hook-on fitting 210 within the hinge slot 534 of the blade fitting 530 and providing relative movement between the hinge pin 218 and the hinge slot 534 until the hinge pin 218 abuts against the semicircular bearing surface 535 of the hinge slot 534 and is locked therein by the hinge lock 536. FIG. 9B shows the hinge lock 536 locking the hinge pin 218 of the conventional handle 200 within the hinge slot 534 of the universal laryngoscope blade 500 in the operating position. Relative rotational movement is provided between the universal laryngoscope blade 500 and the conventional handle 200 such that the hinge slot 534 and the hinge pin 218 are rotated relative to one and other until the body 532 of the blade fitting 530 slides within the seat 219 of the hook-on fitting 210, as shown in FIGS. 8B-9C. After the body 532 of the blade fitting 530 is fully received within the seat 219 of the hook-on fitting 210, the first and second side locks 538a, 538b of the blade fitting 530 respectively engage with the first and second lock slots 216a, 216b of the hook-on fitting 210, as shown in FIG. 9C. With the side locks engaged with the respective lock slots and the hinge lock 536 engaged with the hinge pin 218, the body 532 of the universal laryngoscope blade 500 is locked within the seat 219 of the conventional handle 200 in the operating position, and the laryngoscope is ready-for-use. The one or more cables 523 of the universal laryngoscope blade 500 may be connected to the external device 600 at any time prior to use.

Although FIGS. 8A-9C depict engagement between the universal laryngoscope blade 500 having one or more cables 523 and the conventional handle 200, the invention also includes engagement between the universal laryngoscope blade 500 having the viewer 520' without any direct connection (i.e., cable link) with the external device 600 and the conventional handle 200. That is, the mechanical engagement between the blade fitting 530 of the universal laryngoscope blade 500 and the hook-on fitting 210 of the conventional handle 200 is the same regardless of the type of viewer employed by the universal laryngoscope blade 500. Each universal laryngoscope blade 500 is self-contained in that the universal laryngoscope blade 500 does not require power or light from the conventional handle 200 (although in some embodiments power or light may be provided by an external device 600 other than the conventional handle 200).

Figures 10A, 10B:
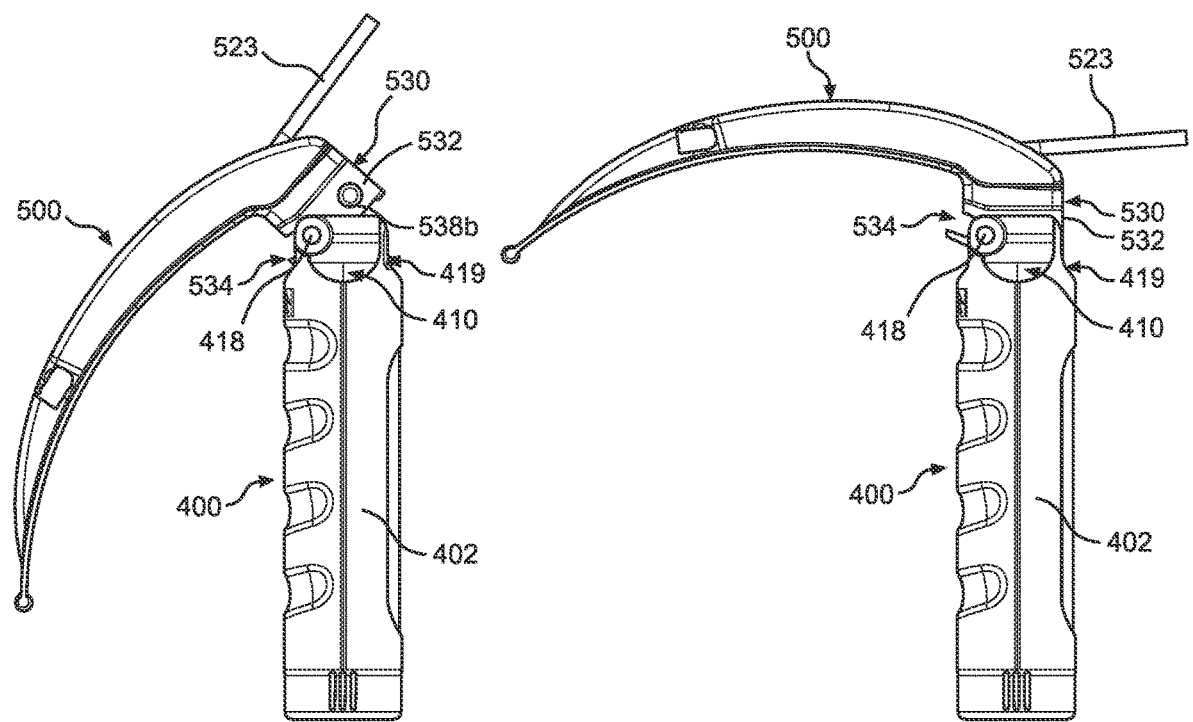
FIG. 10A shows a side view of the universal laryngoscope blade hooked-on to the hinge pin of the fiber-illuminated handle in accordance with aspects of the invention.
FIG. 10B shows a side view of the universal laryngoscope blade engaged with the fiber-illuminated handle in the operating position in accordance with aspects of the invention.
Figure 11A:
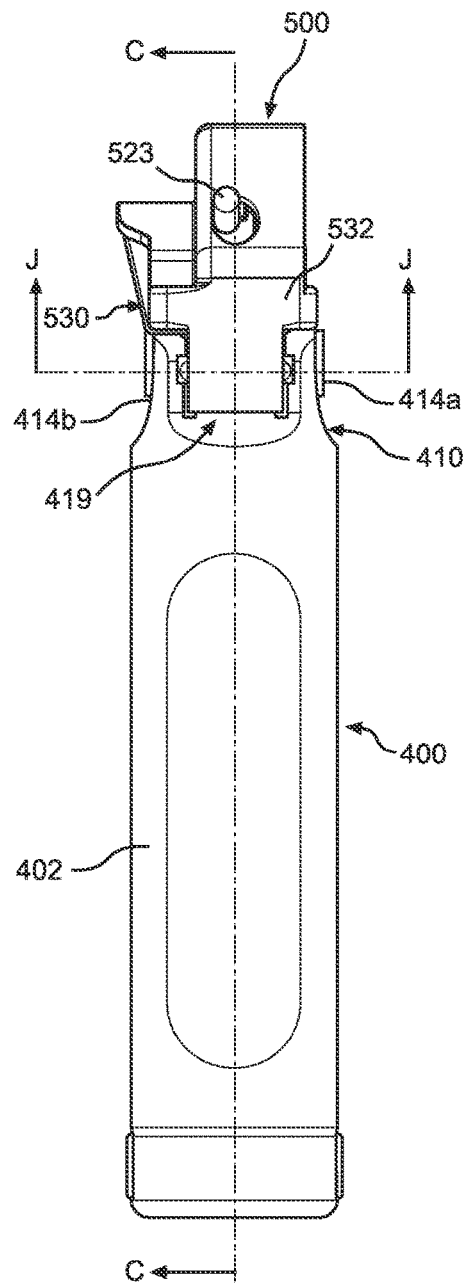
FIG. 11A shows a rear view of the universal laryngoscope blade engaged with the fiber-illuminated handle in the operating position in accordance with aspects of the invention.
Figure 11B:
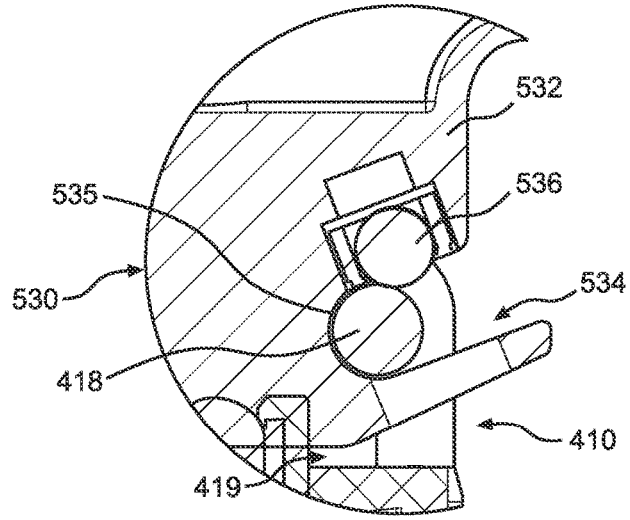
FIG. 11B shows a magnified cross-sectional view of the engagement between blade fitting of the universal laryngoscope blade and the hook-on fitting of the fiber-illuminated handle of FIG. 11A taken along section C-C.
Figure 11C:
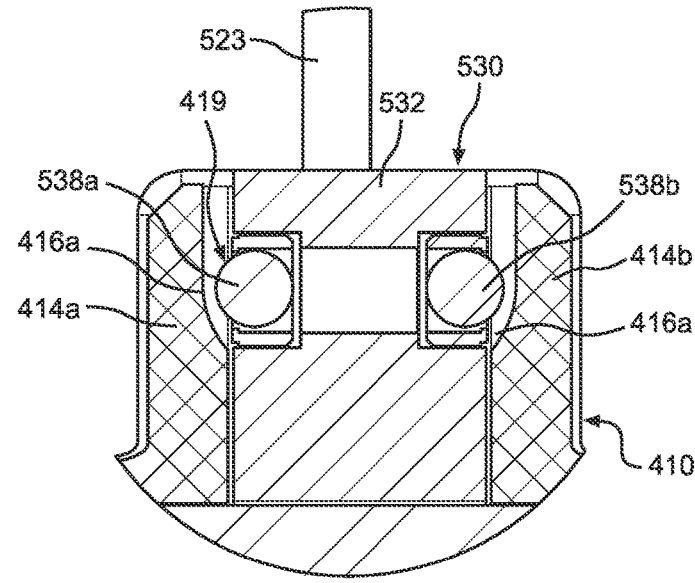
FIG. 11C shows a magnified cross-sectional view of the engagement between the blade fitting of the universal laryngoscope blade and the hook-on fitting of the fiber-illuminated handle of FIG. 11A taken along section J-J.

FIGS. 10A-11C depict engagement of the universal laryngoscope blade 500 and the fiber-illuminated handle 400. FIG. 10A shows a side view of the universal laryngoscope blade 500 hooked-on to the hinge pin 418 of the fiber-illuminated handle 400. FIG. 10B shows a side view of the universal laryngoscope blade 500 engaged with the fiber-illuminated handle 400 in the operating position. FIG. 11A shows a rear view of the universal laryngoscope blade 500 engaged with the fiber-illuminated handle 400 in the operating position. FIG. 11B shows a magnified cross-sectional view of the engagement between blade fitting 530 of the universal laryngoscope blade 500 and the hook-on fitting 410 of the fiber-illuminated handle 400 of FIG. 11A taken along section C-C. FIG. 11C shows a magnified cross-sectional view of the engagement between the blade fitting 530 of the universal laryngoscope blade 500 and the hook-on fitting 410 of the fiber-illuminated handle 400 of FIG. 11A taken along section J-J.

The blade fitting 530 of the universal laryngoscope blade 500 is also configured to engage with the hook-on fitting 410 of the fiber-illuminated handle 400 to lock the universal laryngoscope blade 500 within the seat 419 of the fiber-illuminated handle 400 in an operating position, in which the laryngoscope is ready-for-use. As shown in FIG. 10A, to place the universal laryngoscope blade 500 in the operating position, the blade fitting 530 is first attached to the hook-on fitting 410. The blade fitting 530 is attached to the hook-on fitting 410 of the fiber-illuminated handle 400 by placing the hinge pin 418 of the hook-on fitting 410 within the hinge slot 534 of the blade fitting 530 and providing relative movement between the hinge pin 418 and the hinge slot 534 until the hinge pin 418 abuts against the semicircular bearing surface 535 of the hinge slot 534 and is locked therein by the hinge lock 536. FIG. 11B shows the hinge lock 536 locking the hinge pin 418 of the fiber-illuminated handle 400 within the hinge slot 534 of the universal laryngoscope blade 500 in the operating position. Relative rotational movement is provided between the universal laryngoscope blade 500 and the fiber-illuminated handle 400 such that the hinge slot 534 and the hinge pin 418 are rotated relative to one and other until the body 532 of the blade fitting 530 slides within the seat 419 of the hook-on fitting 410, as shown in FIGS. 10B-11C. After the body 532 of the blade fitting 530 is fully received within the seat 419 of the hook-on fitting 410, the first and second side locks 538a, 538b of the blade fitting 530 respectively engage with the first and second lock slots 416a, 416b of the hook-on fitting 410, as shown in FIG. 11C. With the side locks engaged with the respective lock slots and the hinge lock 536 engaged with the hinge pin 418, the body 532 of the universal laryngoscope blade 500 is locked within the seat 419 of the fiber-illuminated handle 400 in the operating position, and the laryngoscope is ready-for-use. The one or more cables 523 of the universal laryngoscope blade 500 may be connected to the external device 600 at any time prior to use.

Although FIGS. 10A-11C depict engagement between the universal laryngoscope blade 500 having one or more cables 523 and the fiber-illuminated handle 400, the invention also includes engagement between the universal laryngoscope blade 500 having the viewer 520' without any direct connection (i.e., cable link) with the external device 600 and the fiber-illuminated handle 400. That is, the mechanical engagement between the blade fitting 530 of the universal laryngoscope blade 500 and the hook-on fitting 410 of the fiber-illuminated handle 400 is the same regardless of the type of viewer employed by the universal laryngoscope blade 500. Each universal laryngoscope blade 500 is self-contained in that the blade does not require power or light from the fiber-illuminated handle 400 (although in some embodiments power or light may be provided by an external device 600 other than the fiber-illuminated handle 400).

Figure 12A:
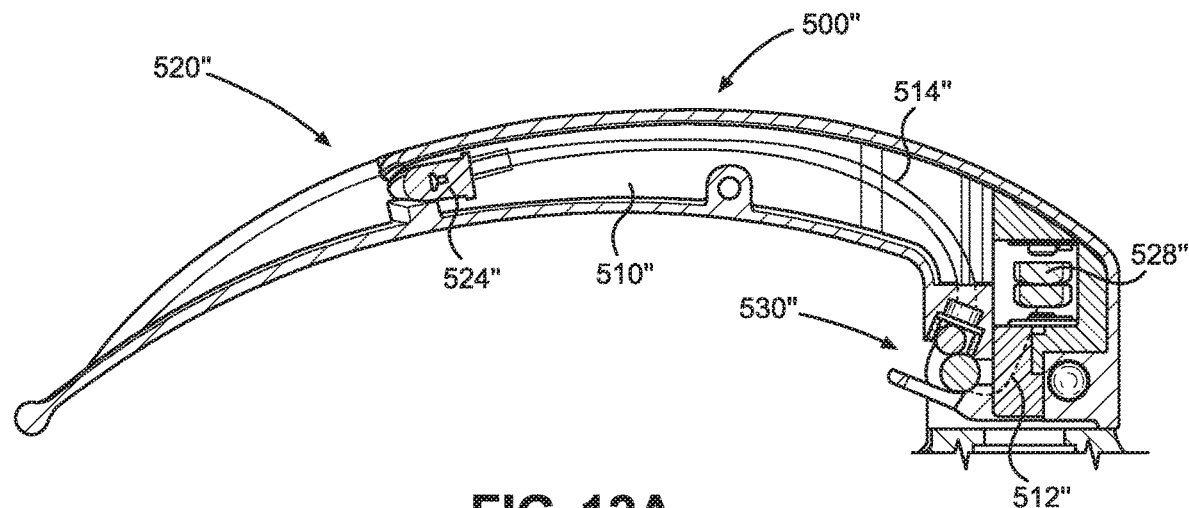
FIG. 12A shows another implementation of a universal laryngoscope blade engaged to a conventional handle in an operating position.
Figure 12B:
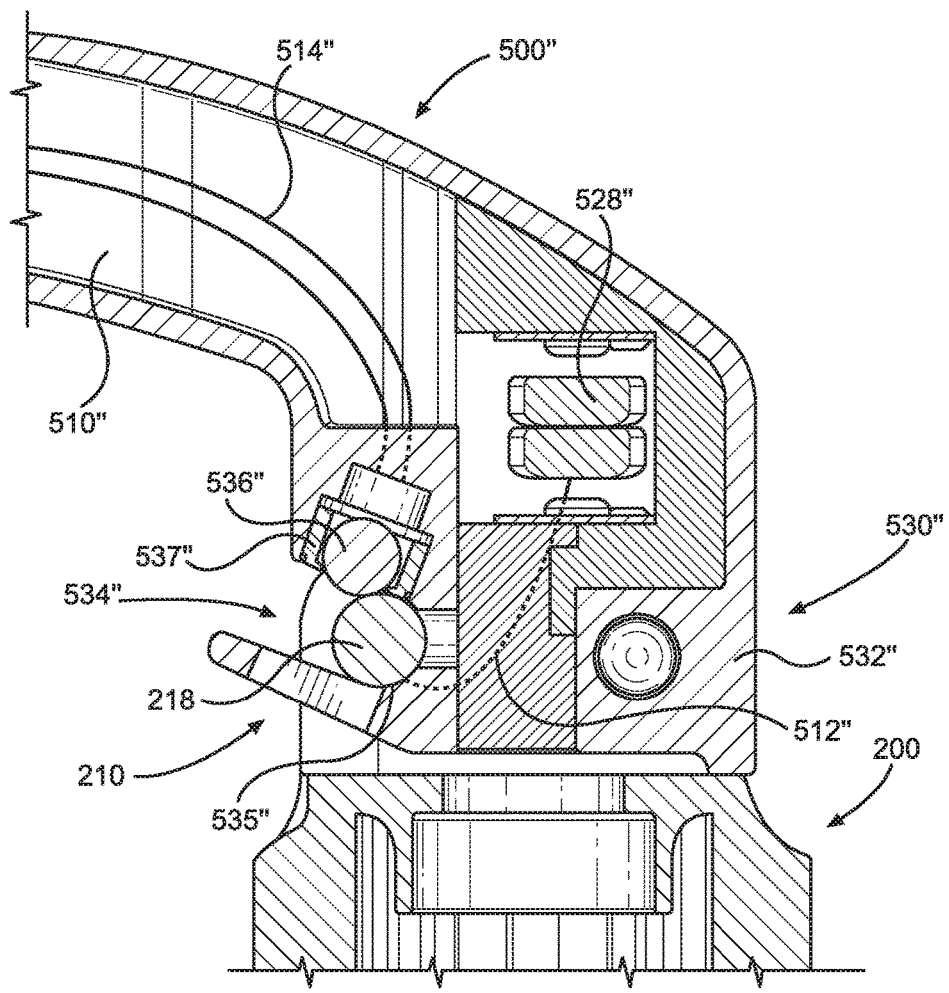
FIG. 12B shows a magnified view of FIG. 12A depicting the blade fitting of the universal laryngoscope blade engaged to a hook-on fitting of the conventional handle in an operating position.

FIGS. 12A-12B show exemplary views of another implementation of a universal laryngoscope blade 500" in accordance with aspects of the present disclosure. The universal laryngoscope blade 500" includes a blade body 510", a viewer 520", a power source 528", and a blade fitting 530". The universal laryngoscope blade 500" may be, entirely or partially, reusable or disposable. The blade body 510" may be the same as the blade body 510 previously discussed in detail above with regards to the other universal laryngoscope blade implementations. For instance, the blade body 510" may be shaped to provide a direct view of a larynx. The blade body 510" may be provided in any number of shapes and sizes depending, e.g., on the size of the patient. The blade body 510" may include a first end and a second end, the power source 528" disposed at the first end, and the second end operable for insertion into the larynx of a patient.

For illustrations purposes, FIG. 12A depicts engagement of the universal laryngoscope blade 500" with the conventional handle 200. In particular, a side view of the universal laryngoscope blade 500" hooked-on to the hinge pin 218 of the conventional handle 200 is illustrated, such that the universal laryngoscope blade 500" is engaged with the conventional handle 200 in the operating position. FIG. 12B shows a magnified view of the engagement between blade fitting 530" of the universal laryngoscope blade 500" and the hook-on fitting 210 of the conventional handle 200.

The viewer 520" is connected to the blade body 510" and is operable to illuminate the larynx when the second end of the blade body 510" is inserted therein. The viewer 520" is operable to function (e.g., emit light, capture at least one image, etc.) independently with each of the conventional handle 200 and the fiber-illuminated handle 400. The viewer 520" may include a lamp 524", such as an LED, that emits light in a direction towards the second end of the blade body 510" to illuminate the second end of the blade body 510" and/or the larynx. Similar to the other implementations discussed above, the lamp 524" may be provided within a housing. The viewer 520" may include a camera that may capture one or more images, from the perspective of an opening of the housing, of the second end of the blade body 510" and/or of the larynx. The viewer 520" may include a power source 528" (e.g., one or more batteries) that supplies power to the lamp 524", camera, etc. The power source 528" may be provided on the blade body 510", such as the first end of the blade body.

The universal laryngoscope blade 500" is configured to be removably connectable, one at a time, to each of the conventional handle 200 and the fiber-illuminated handle 400. The blade fitting 530" of the laryngoscope blade 500" is disposed at the first end of the blade body 510". The blade fitting 530" is configured to be removably connectable, one at a time, to each of the hook-on fitting 210 of the conventional handle 200 and the hook-on fitting 410 of the fiber-illuminated handle 400. Moreover, the blade fitting 530" is removably connectable to and functional with, one at a time, each of the hook-on fitting 210 of the conventional handle 200 and the hook-on fitting 410 of the fiber-illuminated handle 400. In other implementations, the blade fitting 530" may also be adapted for removable connection to, and functionality with, hook-on fittings of other handles that differ from the hook-on fitting 210 of the conventional handle 200 and the hook-on fitting 410 of the fiber-illuminated handle 400 described herein.

The blade fitting 530" of the universal laryngoscope blade 500" includes a body 532", a lock, and a hinge slot 534". The body 532" is similar to the body 532 shown in FIG. 7A and has a thickness $T_U$. The thickness $T_U$ of the body 532" of the universal laryngoscope blade 500" may be greater than the thickness $T_C$ of the body of the conventional blade 100 but less than the thickness $T_F$ of the body 332 of the fiber-illuminated blade 300. For example, the thickness $T_U$ may be between 12.74 and 12.84 mm, and more particularly may be 12.80 mm. According to aspects of the invention, because the thickness $T_U$ of the body 532" of the universal laryngoscope blade 500" may be greater than the thickness $T_C$ of the body 132 of the conventional blade 100 but less than the thickness $T_F$ of the body 332 of the fiber-illuminated blade 300, the body 532" of the universal laryngoscope blade 500" may be small enough to be received within the seat 219 of the conventional handle 200 while large enough to limit excessive play (wobbling) when received within the seat 419 of the fiber-illuminated handle 400. That is, the body 532" of the universal laryngoscope blade 500" may be accommodated within, one at a time, the seat 219 of the conventional handle 200 and the fiber-illuminated handle 400, improving the universality of blade fitting 530" of the universal laryngoscope blade 500".

The lock may include a hinge lock 536" disposed within a top surface of the hinge slot 534". In some implementations, the hinge lock 536" may be disposed within a bottom surface of the hinge slot 534". The lock may also include at least one side lock provided on at least one side of the body 532". The at least one side lock may include first and second side locks respectively provided on opposite sides of the body 532", similar to slide locks 538a, 538b previously described above. The hinge lock 536" and the at least one side lock may be detent mechanisms. The hinge slot 534" may extend into the body 532" at an angle from a front of the body 532" towards a central region of the body 532" and may terminate at a bearing surface 535". The bearing surface 535" may have a semicircular shape having a diameter and a virtual center point about which the bearing surface 535" forms the semicircular shape. The diameter of the semicircular bearing surface 535" of the hinge slot 534", and a width of the hinge slot 534" in general, are dimensioned to accommodate, one at a time, the hinge pin 218 of the conventional handle 200 and the hinge pin 418 of the fiber-illuminated handle 400 such that the respective hinge pin is received within and abuts against the semicircular bearing surface 535". That is, the hinge slot 534" is dimensioned to receive in abutment with the semicircular bearing surface 535", one at a time, the hinge pin 218 of the hook-on fitting 210 of the conventional handle 200 and the hinge pin 418 of hook-on fitting 410 of the fiber-illuminated handle 400. For example, the diameter of the semicircular bearing surface 535" of the hinge slot 534", and a narrowest width of the hinge slot 534" in general, are each at least greater than 4.58 mm.

A center of the hinge lock 536" is spaced forwardly from the virtual center of the semicircular bearing surface 535" by a horizontal distance $H_{UHL}$. The horizontal distance $H_{UHL}$ that the hinge lock 536" of the universal laryngoscope blade 500" is spaced forwardly from the virtual center of the semicircular bearing surface 535" of the universal laryngoscope blade 500" is less than the horizontal distance $H_{FHL}$ that the hinge lock 336 of the fiber-illuminated blade 300 is spaced forwardly from the virtual center of the semicircular bearing surface 335 of the fiber-illuminated blade 300. For example, the horizontal distance $H_{UHL}$ that the hinge lock 536" of the universal laryngoscope blade 500" is spaced forwardly from the virtual center of the semicircular bearing surface 535" of the universal laryngoscope blade 500" may be between 0.86 and 0.90 mm, and more particularly may be 0.88 mm. By locating the hinge lock 536" the horizontal distance $H_{UHL}$ forwardly from the virtual center of the semicircular bearing surface 535", the hinge lock 536" may securely hold, one at a time, the hinge pin 218 of the conventional handle 200 and the hinge pin 418 of the fiber-illuminated handle 400 within the hinge slot 534" of the blade fitting 530". That is, the hinge slot 534" and the hinge lock 536" of the universal laryngoscope blade 500" may accommodate, one at a time, the hinge pin 218 of the conventional handle 200, and the larger hinge pin 418 of the fiber-illuminated handle 400, improving the universality of the blade fitting 530" of the universal laryngoscope blade 500".

As a result of the above-described features and dimensions (e.g., the thickness $T_U$ of the body 532", the width of the hinge slot 534", the diameter of the semicircular bearing surface 535" of the hinge slot 534", the horizontal distance $H_{UHL}$, etc.), the blade fitting 530" of the universal laryngoscope blade 500" may engage with, one at a time, both the hook-on fitting 210 of the conventional handle 200 and the hook-on fitting 410 of the fiber-illuminated handle 400. Accordingly, the universal laryngoscope blade 500" may be attached to, and fully functional with, each of the conventional handle 200 and the fiber-illuminated handle 400 that are dimensioned to conform to the requirements of ISO Standard 7376.

An electrical contact may be provided on the bearing surface 535" of the blade fitting 530". The electrical contact may be in electrical communication with the power source 528" (i.e., batteries) via one or more wires 512" for supplying power to the electrical contact. The electrical contact is further configured to be in electrical communication with the hinge pin 218 of the hook-on fitting 210 when the laryngoscope blade 500" is in the operating position. The hinge pin 218 is metal or another electrically conductive material. An electrical hinge contact 537" may be disposed on a surface of the hinge slot 534" and may be adjacent to the hinge lock 536". The electrical hinge contact 537" is also configured to be in electrical communication with the hinge pin 218 when the laryngoscope blade 500" is in the operating position. The electrical hinge contact 537" may further be in electrical communication with the viewer 520" via one or more wires 514" for supplying power to the viewer, such as to the lamp 524", when the laryngoscope blade 500" is engaged with the conventional handle 200 in the operating position.

Although the universal laryngoscope blade 500" is shown attached to and fully functional with the conventional handle 200 for illustrations purposes, the universal laryngoscope blade 500" is also attachable to and fully functional with the fiber-illuminated handle 400 as previously discussed above. Accordingly, power may be supplied from the power source 528" to the lamp 524" using the existing metal hinge pin 218 of the conventional handle 200 or the metal hinge pin 418 of the fiber-illuminated handle to complete the electrical circuit between the power source and the lamp, thus reducing manufacturing costs as it would be unnecessary to include additional components, such as a microswitch, into the blade.

In some implementations, the hinge lock 536" may be metal or another electrically conductive material, and furthermore may be configured to be in electrical communication with both the hinge pin 218 and the electrical hinge contact 537" when the laryngoscope blade 500" is in the operating position. Thus, a bottom of the body 532" may not include (i.e., may be free of) functional elements (e.g., electrical contacts, light guides, etc.) that would otherwise protrude from the body 532". By not including functional elements on the body 532" of the blade fitting 530", the bottom of the body 532" of the blade fitting 530" may not interfere with functional elements (e.g., electrical contacts, optical pathways, etc.) provided on the hook-on fittings of conventional handles and/or fiber-illuminated handles when connected thereto.

Figure 13:
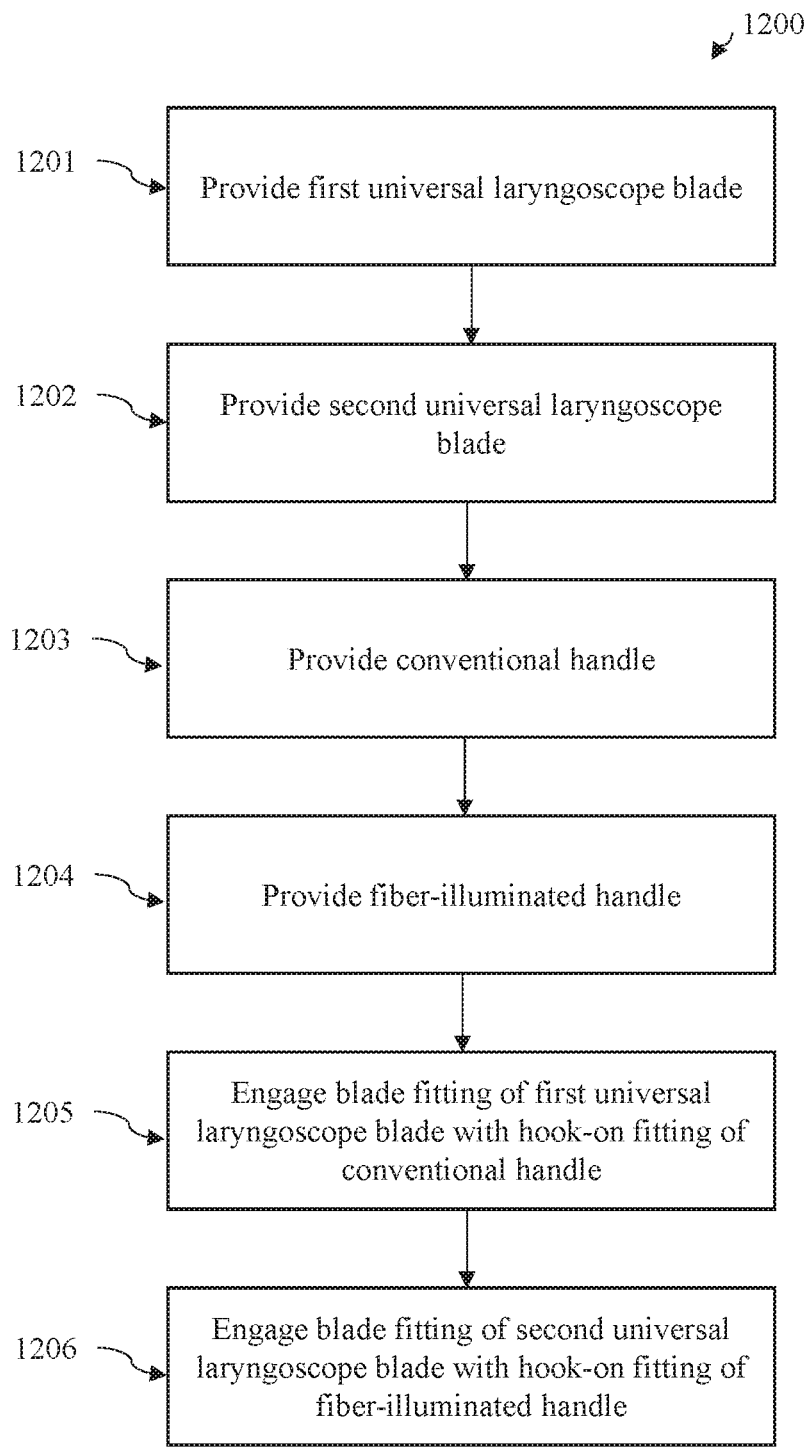
FIG. 13 shows a process of using universal laryngoscope blades in accordance with aspects of the invention.

FIG. 13 shows a process 1200 of using universal laryngoscope blades in accordance with aspects of the invention, including engaging universal laryngoscope blades with a conventional handle and a fiber-illuminated handle (e.g., the conventional handle 200 and the fiber-illuminated handle 400). The process 1200 may include, at a first step 1201, providing a first universal laryngoscope blade. The first universal laryngoscope blade may be any of the universal laryngoscope blades discussed above in accordance with aspects of the invention. For example, the first universal laryngoscope blade may include a blade body shaped to provide a direct view of a larynx. The blade body may include a first end and a second end. The second end may be inserted into the larynx of a patient. The first universal laryngoscope blade may further include a viewer connected to the blade body. The viewer may function independently from each of the conventional handle and the fiber-illuminated handle. That is, the viewer is fully functional (i.e., able to emit light or capture images) without requiring power or light from the conventional handle or the fiber-illuminated handle. The first universal laryngoscope blade may further include a blade fitting disposed at the first end of the blade body.

The process 1200 may include, at a second step 1202, providing a second universal laryngoscope blade. The second universal laryngoscope blade may be any of the universal laryngoscope blades discussed above in accordance with aspects of the invention. For example, the second universal laryngoscope blade may include a blade body shaped to provide a direct view of a larynx. The blade body may include a first end and a second end. The second end may be inserted into the larynx of a patient. The second universal laryngoscope blade may further include a viewer connected to the blade body. The viewer may function independently from each of the conventional handle and the fiber-illuminated handle. That is, the viewer is fully functional (i.e., able to emit light or capture images) without requiring power or light from the conventional handle or the fiber-illuminated handle. The second universal laryngoscope blade may further include a blade fitting disposed at the first end of the blade body. the blade fitting of the second universal laryngoscope blade being identically dimensioned with the blade fitting of the first universal laryngoscope blade. That is, the physical dimensions of each of the above described components of the blade fitting of the universal laryngoscope blade (e.g., the body, the lock, the hinge slot, etc.) may be identical so that the blade fitting of each of the first and second universal laryngoscope blades is the same. "Identically dimensioned," as used herein, means machined to the same size, but includes normal variations resulting from manufacturing tolerances, which would be readily understood by persons having ordinary skill in the art.

The process 1200 may include, at a third step 1203, providing the conventional handle, as discussed above. That is, providing the conventional handle including a hook-on fitting having a seat having a width and a hinge pin having a diameter. The dimensions of the hook-on fitting of the conventional handle may conform to dimensions prescribed for conventional handles in ISO standard 7376.

The process 1200 may include, at a forth step 1204, providing the fiber-illuminated handle, as discussed above. That is, providing the fiber-illuminated handle including a hook-on fitting comprising a seat having a width and a hinge pin having a diameter. The dimensions of the hook-on fitting of the fiber-illuminated handle may conform to dimensions prescribed for fiber-illuminated handles for ISO standard 7376. As is clear from ISO standard 7376, the width of the seat of the fiber-illuminated handle is greater than the width of the seat of the conventional handle, and the diameter of the hinge pin of the fiber-illuminated handle is greater than the diameter of the hinge pin of the conventional handle.

The process 1200 may include, at a fifth step 1205, engaging the blade fitting of the first universal laryngoscope blade with the hook-on fitting of the conventional handle such that the first universal laryngoscope blade is provided in an operating position and ready-for-use. An example of engaging the blade fitting of the first universal laryngoscope blade with the hook-on fitting of the conventional handle is shown, for example, in FIGS. 8A-9C and is discussed in greater detail above.

The process 1200 may include, at a sixth step 1206, engaging the blade fitting of the second universal laryngoscope blade with the hook-on fitting of the fiber-illuminated handle such that the second universal laryngoscope blade is provided in an operating position and ready-for-use. An example of engaging the blade fitting of the second universal laryngoscope blade with the hook-on fitting of the fiber-illuminated handle is shown, for example, in FIGS. 10A-11C and is discussed in greater detail above.

Because the blade fittings of the first and second universal laryngoscope blades are identically dimensioned (including e.g., the thickness $T_U$ of the body, the width of the hinge slot, the diameter of the semicircular bearing surface of the hinge slot, the horizontal distance $H_{UHL}$, the horizontal distance component $D_{UL\_h}$, the vertical distance component $D_{UL\_v}$, etc.), the blade fitting of the universal laryngoscope blades may each engage with, one at a time, both the hook-on fitting of the conventional handle and the hook-on fitting of the fiber-illuminated handle. Further, and as discussed above, the viewers of each of the universal laryngoscope blades are fully functional (i.e., capable of producing/transmitting light/data, capable of capturing one or more images, etc.) without the need for the blade fitting to interface with functional elements (e.g., the electrical contact of the conventional handle or the optical pathway of the fiber-illuminated handle) on the conventional handle or the fiber-illuminated handle. Accordingly, the universal laryngoscope blades may be attached to, and fully functional with, each of the conventional handle and the fiber-illuminated handle that conform to the requirements of ISO Standard 7376. This allows a user to remove handle compatibility from laryngoscope blade purchasing decisions to leverage initial investments in otherwise useful conventional handles and/or fiber-illuminated handles. Universal laryngoscope blades may also reap the benefits of economies of scale, since the universal laryngoscope blades may be produced in greater numbers due to the compatibility with both existing conventional handles and fiber-illuminated handles.

The many features and advantages of the universal laryngoscope blade described herein are apparent from the detailed specification, and thus, the claims cover all such features and advantages within the scope of this application. Further, numerous modifications and variations are possible. As such, it is not desired to limit the universal laryngoscope blade to the exact construction and operation described and illustrated and, accordingly, all suitable modifications and equivalents may fall within the scope of the claims.

What is claimed is:

1. A universal laryngoscope blade comprising:
    a blade body shaped to provide a direct view of a larynx, the blade body including a first end and a second end, the second end being configured for insertion into the larynx;
    a viewer connected to the blade body, the viewer being configured to function independently from each of a conventional handle and a fiber-illuminated handle; and
    a blade fitting disposed at the first end of the blade body, wherein the blade fitting is removably connectable to, one at a time, each of a hook-on fitting of the conventional handle and a hook-on fitting of the fiber-illuminated handle, the hook-on fitting of the conventional handle having at least one physical dimension that is different from at least one physical dimension of the hook-on fitting of the fiber-illuminated handle;
    wherein the blade fitting includes a body and a hinge slot extending into the body at an angle from a front of the body towards a central region of the body and terminating at a semicircular bearing surface having a virtual center point, the body having a thickness that is configured to be received within, one at a time, a seat of the hook-on fitting of the conventional handle and a seat of the hook-on fitting of the fiber-illuminated handle, the seat of the hook-on fitting of the conventional handle having a width that is less than a width of the seat of the hook-on fitting of the fiber-illuminated handle, and
    wherein the blade fitting further includes a hinge lock disposed within a surface of the hinge slot and configured to lock within the hinge slot, one at a time, a hinge pin of the hook-on fitting of the conventional handle and a hinge pin of the hook-on fitting of the fiber-illuminated handle.

2. The universal laryngoscope blade according to claim 1, wherein the thickness of the body is between 12.74 and 12.84 mm.

3. The universal laryngoscope blade according to claim 1, further comprising a power source configured to be in electrical communication with the viewer for supplying power to the viewer when the laryngoscope blade is engaged to one of the conventional handle and the fiber-illuminated handle in an operating position.

4. The universal laryngoscope blade according to claim 3, wherein the blade fitting includes a first electrical contact in electrical communication with the power source and a second electrical contact in electrical communication with the viewer, wherein the first electrical contact is configured to be in electrical communication with the second electrical contact via an electrically conductive hinge pin of one of the conventional handle and the fiber-illuminated handle when the laryngoscope blade is in the operating position.

5. The universal laryngoscope blade according to claim 4, wherein the first electrical contact is in electrical communication with the power source via a first electrical wire, and wherein the second electrical contact is in electrical communication with the viewer via a second electrical wire.

6. The universal laryngoscope blade according to claim 3, wherein a bottom of the body of the blade fitting is free of functional elements.

7. The universal laryngoscope blade according to claim 1, wherein the hinge slot is dimensioned to receive in abutment with the semicircular bearing surface, one at a time, a hinge pin of the hook-on fitting of the conventional handle and a hinge pin of hook-on fitting of the fiber-illuminated handle, the hinge pin of the hook-on fitting of the conventional handle having a diameter that is less than a diameter of the hinge pin of the hook-on fitting of the fiber-illuminated handle.

8. The universal laryngoscope blade according to claim 1, wherein a diameter of the semicircular bearing surface is greater than 4.58 mm.

9. The universal laryngoscope blade according to claim 1, wherein the hinge lock is spaced forwardly from the virtual center point of the semicircular bearing surface by a distance between 0.86 and 0.90 mm.

10. The universal laryngoscope blade according to claim 1, wherein the blade fitting further includes at least one side lock provided on a side of the body, the at least one side lock is configured to lock the body of the blade fitting within, one at a time, the seat of the hook-on fitting of the conventional handle and the seat of the hook-on fitting of the fiber-illuminated handle.

11. The universal laryngoscope blade according to claim 10, wherein a center point of the at least one side lock is spaced rearwardly from the virtual center point of the semicircular bearing surface by a horizontal distance component and spaced below the virtual center point of the semicircular bearing surface by a vertical distance component, the horizontal distance component being 13.0 mm and the vertical distance component being 0.8 mm.

12. The universal laryngoscope blade according to claim 10, wherein the at least one side lock is configured to engage with, one at a time, at least one lock slot of the hook-on fitting of the conventional handle and at least one lock slot of the hook-on fitting of the fiber-illuminated handle.

13. The universal laryngoscope blade according to claim 1, wherein the universal laryngoscope blade is disposable.

14. The universal laryngoscope blade according to claim 1, wherein the universal laryngoscope blade is reusable.

15. The universal laryngoscope blade according to claim 1, wherein the viewer is configured to emit light independently from each of the conventional handle and the fiber-illuminated handle.

16. The universal laryngoscope blade according to claim 1, wherein the viewer is configured to capture at least one image independently from each of the conventional handle and the fiber-illuminated handle.

17. The universal laryngoscope blade according to claim 1, wherein the hook-on fitting of the conventional handle is dimensioned to conform to ISO standard 7376 for conventional handles and the hook-on fitting of the fiber-illuminated handle is dimensioned to conform to ISO standard 7376 for fiber-illuminated handles.

18. The universal laryngoscope blade according to claim 1, wherein the viewer includes:
a lamp configured to emit light into the larynx;
a camera configured to capture at least one image of the larynx; and
at least one cable that provides electronic communication between an external device, and the lamp and the camera.

19. The universal laryngoscope blade according to claim 1, wherein the viewer includes:
a lamp configured to emit light into the larynx;
a camera configured to capture at least one image of the larynx;
a transceiver configured to wirelessly transmit the at least one image to an external device;
a processor configured to control the lamp, the camera, and the transceiver; and
a power source configured to supply power to the lamp, the camera, the transceiver, and the processor.

20. A method of engaging a universal laryngoscope blade with one of a conventional handle and a fiber-illuminated handle, the method comprising:
providing the universal laryngoscope blade according to claim 1;
providing the conventional handle, the conventional handle including a hook-on fitting comprising a seat having a width and a hinge pin having a diameter;
providing the fiber-illuminated handle, the fiber-illuminated handle including a hook-on fitting comprising a seat having a width and a hinge pin having a diameter, the width of the seat of the fiber-illuminated handle being greater than the width of the seat of the conventional handle, the diameter of the hinge pin of the fiber-illuminated handle being greater than the diameter of the hinge pin of the conventional handle;
engaging the blade fitting of the universal laryngoscope blade with one of the hook-on fitting of the conventional handle, such that the universal laryngoscope blade is provided in an operating position and ready-for-use, and the hook-on fitting of the fiber-illuminated handle, such that the second universal laryngoscope blade is provided in an operating position and ready-for-use.

21. The universal laryngoscope blade according to claim 1, further comprising a power source configured to be in electrical communication with the hinge lock when the blade fitting is connected to one of the conventional handle and the fiber-illuminated handle in an operating position.

* * * * *